United States Patent [19]
Ueda et al.

[11] Patent Number: 5,677,408
[45] Date of Patent: Oct. 14, 1997

[54] PROPYLENE ELASTOMER AND PROCESS FOR PREPARATION THEREOF

[75] Inventors: Takashi Ueda; Akira Mizuno, both of Waki-cho; Masaaki Kawasaki, Ichihara; Daisuke Fukuoka, Waki-cho; Yoshihisa Kiso, Waki-cho; Tatsuya Tanizaki, Waki-cho; Mikio Hashimoto, Waki-cho; Masahiro Sugi, Ichihara; Toshiyuki Tsutsui, Waki-cho, all of Japan

[73] Assignee: Mitsui Petrochemical Industries, Ltd., Tokyo, Japan

[21] Appl. No.: 448,502

[22] PCT Filed: Nov. 29, 1994

[86] PCT No.: PCT/JP94/01997

§ 371 Date: Jun. 5, 1995

§ 102(e) Date: Jun. 5, 1995

[87] PCT Pub. No.: WO95/14717

PCT Pub. Date: Jun. 1, 1995

[30] Foreign Application Priority Data

Nov. 29, 1993 [JP] Japan ................ 5-298745

[51] Int. Cl.$^6$ .................. C08F 210/08; C08F 4/642
[52] U.S. Cl. ............. 526/348.6; 526/126; 526/127; 526/132; 526/134; 526/153; 526/160; 526/161; 526/170; 526/943
[58] Field of Search .............. 526/348.6, 160, 526/170, 134, 126, 127, 132, 133, 153, 161

[56] References Cited

U.S. PATENT DOCUMENTS

| | | |
|---|---|---|
| 4,168,361 | 9/1979 | Oda et al. |
| 5,081,322 | 1/1992 | Winter et al. |
| 5,336,746 | 8/1994 | Tsutsui et al. ............... 526/348.6 |
| 5,455,365 | 10/1995 | Winter et al. ............... 526/160 X |
| 5,491,207 | 2/1996 | Hoel ........................... 526/348.6 X |
| 5,504,172 | 4/1996 | Imuta et al. ............... 526/160 X |

FOREIGN PATENT DOCUMENTS

| | | |
|---|---|---|
| 0384264 | 2/1990 | European Pat. Off. |
| 0395055 | 10/1990 | European Pat. Off. |
| 0412416 | 2/1991 | European Pat. Off. |
| 0495099 | 7/1992 | European Pat. Off. |
| 2375262 | 12/1977 | France . |
| 6049120 | 2/1994 | Japan . |
| 6157660 | 6/1994 | Japan . |
| 6157661 | 6/1994 | Japan . |
| 6172414 | 6/1994 | Japan . |
| 6172433 | 6/1994 | Japan . |
| 6271622 | 9/1994 | Japan . |
| 6287224 | 10/1994 | Japan . |
| 6340684 | 12/1994 | Japan . |

*Primary Examiner*—Fred Teskin
*Attorney, Agent, or Firm*—Sherman And Shalloway

[57] ABSTRACT

The novel propylene elastomer according to the invention contains (1) units derived from propylene in amounts of 50 to 95% by mol and units derived from 1-butene in amounts of 5 to 50% by mol, and has (2) triad tacticity (mm fraction), determined by the $^{13}$C-NMR spectrum (hexachlorobutadiene solution, based on tetramethylsilane), of not less than 90%, (3) an intrinsic viscosity (in decalin at 135° C.) of 0.1 to 12 dl/g, (4) a molecular weight distribution (Mw/Mn) of not more than 3 and (5) a randomness parameter B value of 1.0 to 1.5, preferably 1.0 to 1.3. In addition, the elastomer desirably has properties that (6) the elastomer has a melting point Tm of 60° to 140° C., and the melting point Tm and a 1-butene constituent unit content M (% by mol) in the elastomer satisfy the relation $-2.6M+130 \leq Tm \leq -2.3M+155$, and (7) a crystallinity C of the elastomer measured by X-ray diffractometry and the 1-butene constituent unit content M (% by mol) satisfy the relation $C \leq -1.5M+75$. Such propylene elastomer is excellent in rigidity, heat resistance, scratch resistance, transparency, heat sealing properties and blocking resistance. The propylene elastomer can be prepared using a specific transition metal compound catalyst.

8 Claims, No Drawings

PROPYLENE ELASTOMER AND PROCESS FOR PREPARATION THEREOF

This application is based on International Application PCT/JP94/01997, filed Nov. 29, 1994.

TECHNICAL FIELD

The present invention relates to a novel propylene elastomer excellent in rigidity, heat resistance, scratch resistance, transparency, heat sealing properties and blocking resistance.

BACKGROUND ART

Because of their excellent scratch resistance, transparency, heat resistance and heat sealing properties, propylene elastomers are used for films and sheets.

Of various propylene elastomers, propylene elastomers which are copolymers of propylene and 1-butene have been conventionally prepared using solid titanium catalysts or metallocene catalysts comprising metallocene compounds such as zirconium and hafnium and alkylaluminoxane.

However, the conventional propylene elastomers prepared as above are not always satisfactory in heat sealing properties, blocking resistance and heat resistance. Therefore, the advent of a propylene elastomer excellent in not only shock-absorbing properties, heat resistance, transparency and rigidity but also heat sealing properties and blocking resistance has been desired.

Under the circumstances, the present inventors have studied on the propylene elastomers which are copolymers of propylene and 1-butene. As a result, they have found that a propylene elastomer having a high triad tacticity of the head-to-tail enchained propylene unit sequences (the sequences are formed from head-to-tail enchained propylene units, and all the branch directions of the methyl groups are the same) and having high stereoregularity exhibits the above-mentioned excellent properties. They have also found that such propylene elastomer can be efficiently prepared by the use of a specific metallocene compound catalyst component, and accomplished the present invention.

The present applicant has already disclosed a propylene elastomer in which propylene and other α-olefin are head-to-tail enchained regularly in Japanese Patent Laid-Open Publication No. 119212/1987. This propylene elastomer is prepared by the use of a metallocene compound such as ethylenebis(4,5,6,7-tetrahydro-1-indenyl)zirconium dichloride, and it has a higher melting point as compared with the propylene elastomer of the present invention if they are the same in the monomer composition (comonomer ratio).

DISCLOSURE OF INVENTION

The propylene elastomer of the invention has the following properties:

(1) the elastomer contains units derived from propylene in amounts of 50 to 95% by mol and units derived from 1-butene in amounts of 5 to 50% by mol;

(2) when (i) head-to-tail enchained propylene unit triad sequences or (ii) propylene unit-butene unit triad sequences consisting of head-to-tail enchained propylene units and butene units and containing propylene units as the second units are measured on the side chain methyl groups of the propylene units of the second units in the triad sequences using $^{13}$C-NMR spectrum (hexachlorobutadiene solution, based on tetramethylsilane), the area of peaks shown in the region of 21.0 to 21.9 ppm is not less than 90% based on the total area of all peaks shown in the region of 19.5 to 21.9 ppm being 100%;

(3) the elastomer has an intrinsic viscosity, as measured in Decalin at 135° C., of 0.1 to 12 dl/g;

(4) the elastomer has a molecular weight distribution (Mw/Mn), as measured by gel permeation chromatography (GPC), of not more than 3; and (5) the elastomer has a parameter B value, which indicates randomness of the copolymerized monomer sequence distribution, of 1.0 to 1.5.

In the propylene elastomer of the invention, the parameter B value, which indicates randomness of the copolymerized monomer sequence distribution, is preferably 1.0 to 1.3.

In addition to the properties (1) to (5), the propylene elastomer of the invention is desired to further have the following properties:

(6) the elastomer has a melting point Tm, as measured by a differential scanning calorimeter, of 60° to 140° C., and the melting point Tm and a 1-butene constituent unit content M (% by mol) in the elastomer satisfy the following relation:

$$-2.6M+130 \leq Tm \leq -2.3M+155$$

and (7) a crystallinity C of the elastomer, as measured by X-ray diffractometry, and a 1-butene constituent unit content M (% by mol) in the elastomer satisfy the following relation:

$$C \leq -1.5M+75$$

Such a propylene elastomer of the invention as mentioned above is obtained by copolymerizing propylene and 1-butene in the presence of an olefin polymerization catalyst comprising:

[A] a transition metal compound represented by the following formula [I]:

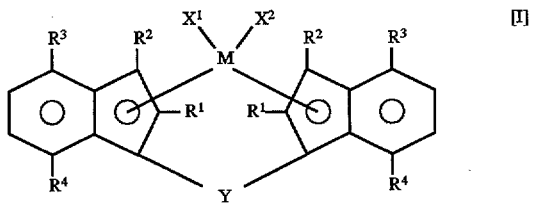

wherein M is a transition metal of Group IVa, Group Va or Group VIa of the periodic table, $R^1$ and $R^2$ are each a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group, $R^3$ is a secondary or tertiary alkyl group of 3 to 20 carbon atoms or an aromatic group, $R^4$ is a hydrogen atom or an alkyl group of 1 to 20 carbon atoms, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, SO—, —S$_2$—, —NR$^5$—, —P(R$^5$)—, —P(O)(R$^5$)—, —BR$^5$— or —AlR$^5$— (wherein R$^5$ is a hydrogen atom, a halogen atom, a hydrocarbon group of 1 to 20 carbon atoms or a halogenated hydrocarbon group of 1 to 20 carbon atoms);

and

[B] [B-1] an organoaluminum oxy-compound, and/or
[B-2] a compound which reacts with the transition metal compound [A] to form an ion pair;

and if desired

[C] an organoaluminum compound.

In the formula [I] representing the transition metal compound [A], R$^1$ is preferably a methyl group.

In the invention, also a transition metal compound [A] represented by the above formula [I] wherein R$^1$ is a hydrocarbon group of 2 to 6 carbon atoms is preferably employed.

BEST MODE FOR CARRYING OUT THE INVENTION

The propylene elastomer according to the invention will be described in detail hereinafter.

(1) The propylene elastomer of the invention is a random copolymer of propylene and 1-butene, and this elastomer contains units derived from propylene in amounts of 50 to 95% by mol, preferably 60 to 93% by mol, more preferably 70 to 90% by mol, and contains units derived from 1-butene in amounts of 5 to 50% by mol, preferably 7 to 40% by mol, more preferably 10 to 30% by mol.

This propylene elastomer may further contain units derived from other olefins than propylene and 1-butene in small amounts, for example, not more than 10% by mol, preferably not more than 5% by mol.

(2) Triad tacticity (mm fraction) of propylene elastomer

The stereoregularity of the propylene elastomer according to the invention can be evaluated by triad tacticity (mm fraction).

When head-to-tail enchained three propylene unit sequences in the polymer chain are expressed by a surface zigzag structure, the mm fraction is defined as a proportion of the propylene unit sequences having the same branch directions of the methyl groups and can be determined using the $^{13}$C-NMR spectrum.

For determining the mm fraction from the $^{13}$C-NMR spectrum, the mm fraction of (i) head-to-tail enchained propylene unit triad sequences and the mm fraction of (ii) propylene unit-butene unit triad sequences consisting of propylene units of head-to-tail enchained propylene units and butene units and containing propylene units as the second units are measured as the mm fraction of the propylene unit-containing triad sequences present in the polymer chains.

The mm fraction can be determined from the peak intensities of the side chain methyl groups of the second units (propylene units) in the triad sequences (i) and (ii). Determination of the mm fraction is described below in detail.

The $^{13}$C-NMR of the propylene elastomer can be measured as follows. In a sample tube, the propylene elastomer is completely dissolved in hexachlorobutadiene containing a small amount of deuterated benzene as a lock solvent, and the $^{13}$C-NMR spectrum is measured by proton complete decoupling at 120° C. under the measuring conditions of a flip angle of 45° and a pulse interval of not shorter than 3.4 T$_1$ (T$_1$: longest time among the spin-lattice relaxation time of methyl groups). Since T$_1$ of the methylene group and T$_1$ of the methine group are shorter than that of the methyl group, the magnetization recovery of all the carbon groups in the sample is not less than 99% under the above conditions. As for the chemical shift, the methyl carbon peak of the third unit in the head-to-tail enchained propylene unit pentad sequence (mmmm) is set to 21.593 ppm on the basis of tetramethylsilane, and other carbon peaks are determined based on this peak.

In the $^{13}$C-NMR spectrum of the propylene elastomer thus measured, the methyl carbon region wherein the side chain methyl groups of the propylene units are observed (about 19.5 to 21.9 ppm) are classified into:

a first peak region (about 21.0 to 21.9 ppm),
a second peak region (about 20.2 to 21.0 ppm), and
a third peak region (about 19.5 to 20.2 ppm).

In each of the above regions, peaks of the side chain methyl groups of the second units (propylene units) in the head-to-tail enchained three molecule sequences (i) and (ii) set forth in Table 1 are observed.

TABLE 1

| | Methyl carbon region (19.5 ~ 21.9 ppm) | | |
|---|---|---|---|
| Shift value | First region (ppm) 21.0 ~ 21.9 | Second region (ppm) 20.2 ~ 21.0 | Third region (ppm) 19.5 ~ 20.2 |
| Hand-to-tail enchainment | | | |
| Sequence (i) Sequence (ii) | PPP (mm) PPB (mm) BPB (mm) | PPP (mr) PPB (mr) BPB (mr) PPB (rr) BPB (rr) | PPP (rr) |

In the above table, P indicates a unit derived from propylene, and B indicates a unit derived from 1-butene.

With regard to the triad sequences (i) consisting of only propylene units, i.e., PPP (mm), PPP (mr) and PPP (rr), among the head-to-tail enchained triad sequences (i) and (ii) set forth in Table 1, the directions of the methyl groups are illustrated below by the surface zigzag structures. These PPP sequences apply correspondingly to the mm, mr and rr triad sequences (PPB, BPB) (ii) which contain butene unit.

PPP (mm): 
$$-(CH-CH_2)-(CH-CH_2)-(CH-CH_2)-$$
with CH$_3$ above each CH

PPP (mr):
$$-(CH-CH_2)-(CH-CH_2)-(CH-CH_2)-$$
with CH$_3$ above first two, CH$_3$ below third PPP (rr):
$$-(CH-CH_2)-(CH-CH_2)-(CH-CH_2)-$$
with CH$_3$ above first and third, CH$_3$ below second In the first region, the methyl groups of the second units (propylene units) in the mm triad sequences PPP, PPB and BPB resonate.

In the second region, the methyl groups of the second units (propylene units) in the mr triad sequences PPP, PPB and BPB and the methyl groups of the second units (propylene units) in the rr triad sequences PPB and BPB resonate.

In the third region, the methyl groups of the second units (propylene units) in the rr triad sequences PPP resonate.

Accordingly, when (i) the head-to-tail enchained propylene unit triad sequences and (ii) the propylene unit-butene unit triad sequences consisting of head-to-tail enchained propylene units and butene units and containing propylene units as the second units are measured on the side chain methyl groups of the propylene units of the second units in the triad sequences using the $^{13}$C-NMR spectrum (hexachlorobutadiene solution, based on tetramethylsilane), the triad tacticity (mm fraction) of the propylene elastomer can be determined as a proportion (percentage) of the area of the peaks shown in the region of 21.0 to 21.9 ppm (the first region) based on the total area of the peaks shown in the region of 19.5 to 21.9 ppm (methyl carbon region) being 100%, in accordance with the following equation.

$$\text{mm Fraction} (\%) = \frac{\text{Methyl group intensity [PPP (mm) + PPB (mm) + BPB (mm)]}}{\text{Methyl group intensity [PPP (mm) + PPB (mm) + BPB (mm) + PPP (mr) + PPB (mr) + BPB (mr) + PPP (rr) + PPB (rr) + BPB (rr)]}} \times 100$$

The mm fraction of the propylene elastomer according to the invention determined as above is not less than 90%, preferably not less than 92%, more preferably not less than 94%.

Other than the above-mentioned head-to-tail enchained triad sequences (i) and (ii), the propylene elastomer has small amounts of partial structures which contain regio-irregular units represented by the following structures (iii), (iv) and (v), and the peaks derived from the side chain methyl groups of the propylene units having such structures (iii), (iv) and (v) are observed in the above-mentioned methyl carbon region (19.5 to 21.9 ppm).

chain methyl group in the propylene-propylene-ethylene sequence) (20.7 ppm or thereabout), a peak based on the EPE-methyl group (side chain methyl group of the ethylene-propylene-ethylene sequence) (19.8 ppm or thereabout) and peaks based on the methyl group C, the methyl group D, the methyl group D', the methyl group E and the methyl group E'.

As described above, the peaks based on the methyl groups other than those of the head-to-tail triad sequences (i) and (ii) are observed, but in the determination of the mm fraction using the above equation, they are corrected as follows.

The peak area based on the PPE-methyl group can be determined from the peak area of the PPE-methine group (resonance at 30.6 ppm or thereabout), and the peak area based on the EPE-methyl group can be determined from the peak area of the EPE-methine group (resonance at 32.9 ppm or thereabout).

The peak area based on the methyl group C can be determined from the peak area of the adjoining methine group (resonance at 31.3 ppm or thereabout).

The peak area based on the methyl group D can be determined from ½ of the total peak area of the peaks based on the αβ methylene carbon in the above structure (iv) (resonance at 34.3 ppm or thereabout and resonance at 34.5 ppm or thereabout), and the peak area based on the methyl group D' can be determined from the area of the peak based on the adjoining methine group (resonance at 33.3 ppm or thereabout) of the methyl group E' in the above structure (v).

The peak area based on the methyl group E can be determined from the peak area of the adjoining methine carbon (resonance at 33.7 ppm or thereabout), and the peak area of the methyl group E' can be determined from the peak area of the adjoining methine carbon (resonance at 33.3 ppm or thereabout).

Accordingly, the peak area of the methyl groups based on the head-to-tail enchained propylene unit triad sequences (i)

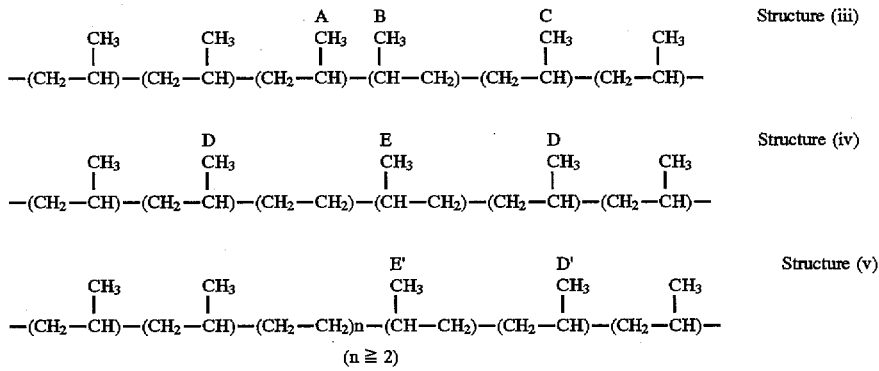

Of the methyl groups derived from the above structures (iii), (iv) and (v), the methyl carbon A and the methyl carbon B resonate at 17.3 ppm and 17.0 ppm, respectively, and consequently the peaks based on the carbon A and the carbon B do not appear in the above-mentioned first to third regions (19.5 to 21.9 ppm). Further, the carbon A and the carbon B have no relation to the head-to-tail enchained propylene triad sequence, so that they do not need to be taken into account in the calculation of the triad tacticity (mm fraction).

The peak based on the methyl carbon C, the peak based on the methyl carbon D and the peak based on the methyl carbon D' appear in the second region, and the peak based on the methyl carbon E and the peak based on the methyl carbon E' appear in the third region.

In the first to third methyl carbon regions, accordingly, there appear a peak based on the PPE-methyl group (side and (ii) can be determined by subtracting the peak area of the above methyl groups from the total peak area of the peaks in the second and third regions.

Thus, the peak area of the methyl groups based on the head-to-tail enchained propylene unit triad sequences (i) and (ii) can be evaluated, and consequently the mm fraction can be calculated in accordance with the above equation.

The carbon peaks in the spectrum can be assigned with reference to a literature "Polymer", 30, 1350 (1989).

(3) Intrinsic viscosity [η]

The intrinsic viscosity [η] of the propylene elastomer according to the invention, as measured in decalin at 135° C., is in the range of 0.1 to 12 dl/g, preferably 0.5 to 12 dl/g, more preferably 1 to 12 dl/g.

(4) Molecular weight distribution

The molecular weight distribution (Mw/Mn) of the propylene elastomer according to the invention, as measured by gel permeation chromatography GPC, is not more than 3, preferably in the range of 2.0 to 3.0, more preferably 2.0 to 2.5.

(5) Randomness

The parameter B value of the propylene elastomer according to the invention, which indicates randomness of the copolymerized monomer distribution, is in the range of 1.0 to 1.5, preferably 1.0 to 1.3, more preferably 1.0 to 1.2.

The parameter B value was proposed by B. D. Cole-man and T. G. Fox (J. Polym. Sci., A1, 3188 (1963)), and this parameter is defined as follows.

$$B = P_{12} / (2P_1 \cdot P_2)$$

wherein $P_1$ and $P_2$ are a first monomer content fraction and a second monomer content fraction, respectively, and $P_{12}$ is a proportion of the first monomer-second monomer sequences to all the two molecule sequences.

In the case of B=1, Bernoulli's statistics apply to the copolymer; in the case of B<1, the copolymer tends to be block; and in the case of B>1, the copolymer tends to be alternating.

In addition to the properties mentioned above, the propylene elastomer of the invention desirably has the following properties.

(6) The melting point Tm measured by a differential scanning calorimeter is in the range of 60° to 140° C., preferably 80° to 130° C., and the melting point Tm and the 1-butene constituent unit content M (% by mol) satisfy the following relation.

$$-2.6M + 130 \leq Tm \leq -2.3M + 155$$

(7) The crystallinity C measured by X-ray diffractometry and the 1-butene constituent unit content M (% by mol) satisfy the following relation.

$$C \geq -1.5M + 75$$

(8) The propylene elastomer of the invention sometimes has small amounts of structures which contain hetero bond units (regio-irregular units) based on 2,1-insertion or 1,3-insertion of propylene present in the propylene sequences.

In the polymerization, propylene is generally 1,2-inserted (methylene side is bonded to catalyst) to form the aforesaid head-to-tail enchained propylene sequence, but in rare cases propylene is 2,1-inserted or 1,3-inserted. The 2,1-inserted propylenes or the 1,3-inserted propylenes form regio-irregular units represented by the aforementioned structures (iii), (iv) and (v) in the polymer. The proportions of the 2,1-insertions and the 1,3-insertions of propylene in the polymer constituent units can be determined by the following equation using a $^{13}$C-NMR spectrum similarly to the aforesaid triad tacticity, with reference to "Polymer", 30, 1350 (1989).

The proportion of the regio-irregular units based on the 2,1-insertions of propylene can be determined by the following equation.

$$\text{Proportion of regio-irregular units based on 2,1-insertions} = \frac{\{0.5 I\alpha\beta \text{ (Structure (iii), (v))} + 0.25 I\alpha\beta \text{ (Structure (iv))}\}}{I\alpha\alpha + I\alpha\beta \text{ (Structure (iii), (v))} + 0.5(I\alpha\gamma + I\alpha\beta(\text{Structure (iv)}) + I\alpha\delta)} \times 100$$

When it is difficult to directly determine the area of $I\alpha\beta$ or the like from the spectrum because of, for example, overlapping of the peaks, correction can be made using the carbon peaks having corresponding areas.

The propylene elastomer according to the invention may contain the above-determined hetero bond units based on the 2,1-insertions of propylene present in the propylene sequences in amounts of not less than 0.01%, specifically 0.01 to 0.3%, based on the whole propylene units.

The proportion of the regio-irregular units based on the 1,3-insertions of propylene in the propylene elastomer can be determined from the $\beta\gamma$ peak (27.4 ppm or thereabout). In the propylene elastomer of the invention, the proportion of the hetero bonds based on the 1,3-insertions of propylene may be not more than 0.05%.

The propylene elastomer of the invention mentioned above can be obtained by copolymerizing propylene and 1-butene in the presence of an olefin polymerization catalyst comprising:

[A] a transition metal compound described later, and

[B] [B-1] an organoaluminum oxy compound and/or

[B-2] a compound which reacts with the transition metal compound [A] to form an ion pair, and if desired

[C] an organoaluminum compound.

The olefin polymerization catalyst used for the invention is described below.

The transition metal compound [A] (hereinafter sometimes referred to as "component [A]") for forming the olefin polymerization catalyst used for the invention is represented by the following formula [I]:

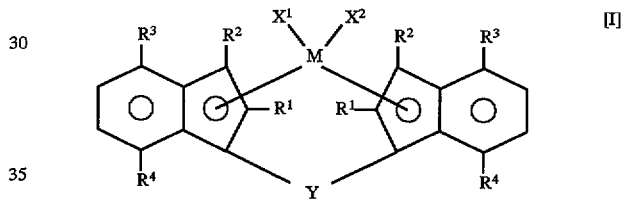

wherein M is a transition metal of Group IVa, Group Va or Group VIa of the periodic table. Examples thereof include titanium, zirconium, hafnium, vanadium, niobium, tantalum, chromium, molybdenum and tungsten. Of these, preferred are titanium, zirconium and hafnium. Particularly preferred is zirconium.

Substituents $R^1$ and $R^2$ $R^1$ and $R^2$ are each a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group.

Examples of the halogens include fluorine, chlorine, bromine and iodine.

Examples of the hydrocarbon groups of 1 to 20 carbon atoms include alkyl groups, such as methyl, ethyl, propyl, butyl, hexyl, cyclohexyl, octyl, nonyl, dodecyl, icosyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenyl, naphthyl, methylnaphthyl, anthracenyl and phenanthryl.

Examples of the halogenated hydrocarbon groups include those obtained by substituting the above-mentioned hydrocarbon groups with halogen atoms.

Examples of the silicon-containing substituents include monohydrocarbon-substituted silyls, such as methylsilyl and phenylsilyl; dihydrocarbon-substituted silyls, such as dimethylsilyl and diphenylsilyl; trihydrocarbon-substituted silyls, such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ethers of hydrocarbon-substituted silyls, such as trimethylsilyl ether; silicon-substituted alkyl groups, such as trimethylsilylmethyl; and silicon-substituted aryl groups, such as trimethylphenyl.

Examples of the oxygen-containing substituents include hydroxyl groups; alkoxy groups, such as methoxy, ethoxy, propoxy and butoxy; aryloxy groups, such as phenoxy, methylphenoxy, dimethylphenoxy and naphthoxy; and arylalkoxy groups, such as phenylmethoxy and phenylethoxy.

Examples of the sulfur-containing groups include substituents obtained by replacing oxygen with sulfur in the above-exemplified oxygen-containing groups.

Examples of the nitrogen-containing groups include amino groups; alkylamino groups, such as methylamino, dimethylamino, diethylamino, dipropylamino, dibutylamino and dicyclohexylamino; and arylamino groups and alkylarylamino groups, such as phenylamino, diphenylamino, ditolylamino, dinaphthylamino and methylphenylamino.

Examples of the phosphorus-containing groups include phosphino groups, such as dimethylphosphino and diphenylphosphino.

Of these, preferred as $R^1$ are hydrogen, methyl, hydrocarbon groups of 2 to 6 carbon atoms and aromatic groups, and particularly preferred are methyl and hydrocarbon groups of 2 to 6 carbon atoms.

As $R^2$, preferred are hydrogen and hydrocarbon groups, and particularly preferred is hydrogen.

Substituent $R^3$ $R^3$ is a hydrocarbon group of 1 to 20 carbon atoms or a group obtained by substituting said hydrocarbon group with a halogen atom or a silicon-containing group, and is preferably a secondary or tertiary alkyl group of 3 to 20 carbon atoms or an aromatic group.

Examples of the secondary or tertiary alkyl groups include i-propyl, i-butyl, sec-butyl, tert-butyl, 1,2-dimethylpropyl, 2,3-dimethylbutyl, iso-pentyl, tert-pentyl, neopentyl, cyclopentyl, cyclohexyl, 4-methylcyclohexyl, iso-hexyl, norbornyl and adamantyl.

Examples of the aromatic groups include aryl groups, such as phenyl, tolyl, dimethylphenyl, trimethylphenyl, ethylphenyl, propylphenyl, biphenyl, α- or β-naphthyl, methylnaphthyl, anthracenyl, phenanthryl, benzylphenyl, pyrenyl, acenaphthyl, phenalenyl, aceanthrylenyl, tetrahydronaphthyl, indanyl and biphenyl; and arylalkyl groups, such as benzyl, phenylethyl, phenylpropyl and tolylmethyl. These groups may contain double or triple bond.

Further, these groups may be substituted with such halogen atoms and silicon-containing groups as described for $R^1$.

Substituent $R^4$ $R^4$ is a hydrogen atom or an alkyl group of 1 to 20 carbon atoms.

Examples of the alkyl groups include chain and cyclic alkyl groups, such as methyl, ethyl, n-propyl, i-propyl, n-butyl, i-butyl, sec-butyl, tert-butyl, pentyl, hexyl, cyclohexyl, heptyl, octyl, nonyl, dodecyl, icosyl, norbornyl and adamantyl.

These groups may be substituted with such halogen atoms and silicon-containing groups as described for $R^1$.

$X^1$ and $X^2$ $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group.

Examples of the halogen atoms, the oxygen-containing groups, the hydrocarbon groups of 1 to 20 carbon atoms and the halogenated hydrocarbon groups of 1 to 20 carbon atoms are the same as those described for $R^1$.

Examples of the sulfur-containing groups include the same groups as described for $R^1$; sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzenesulfonato; and sulfinato groups, such as methylsulfinato, phenylsulfinato, benzenesulfinato, p-toluenesulfinato, trimethylbenzenesulfinato and pentafluorobenzenesulfinato.

Y

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, SO—, —$S_2$—, —$NR^5$—, —$P(R^5)$—, —$P(O)(R^5)$—, —$BR^5$— or —$AlR^5$— ($R^5$ is a hydrogen atom, a halogen atom, a hydrocarbon group of 1 to 20 carbon atoms or a halogenated hydrocarbon group of 1 to 20 carbon atoms).

More specifically, there can be mentioned:

divalent hydrocarbon groups of 1 to 20 carbon atoms, such as alkylene groups (e.g., methylene, dimethylmethylene, 1,2-ethylene, dimethyl-1,2-ethylene, 1,3-trimethylene, 1,4-tetramethylene, 1,2-cyclohexylene and 1,4-cyclohexylene) and arylalkylene groups (e.g., diphenylmethylene and diphenyl-1,2-ethylene);

divalent halogenated hydrocarbon groups obtained by halogenating the above-exemplified divalent hydrocarbon groups of 1 to 20 carbon atoms, such as chloromethylene;

divalent silicon-containing groups, such as alkylsilylene, alkylarylsilylene and arylsilylene groups (e.g., methylsilylene, dimethylsilylene, diethylsilylene, di(n-propyl)silylene, di(i-propyl)silylene, di(cyclohexyl) silylene, methylphenylsilylene, diphenylsilylene, di(p-tolyl)silylene and di(p-chlorophenyl)silylene) and alkyldisilyl, alkylaryldisilyl and aryldisilyl groups (e.g., tetramethyl-1,2-disilyl and tetraphenyl-1,2-disilyl);

divalent germanium-containing groups obtained by replacing silicon with germanium in the above-exemplified divalent silicon-containing groups; and divalent tin-containing groups obtained by replacing silicon with tin in the above-exemplified divalent silicon-containing groups.

$R^5$ is the same halogen atom, hydrocarbon group of 1 to 20 carbon atoms or halogenated hydrocarbon group of 1 to 20 carbon atoms as described for $R^1$.

Of these, preferred are divalent silicon-containing groups, divalent germanium-containing groups and divalent tin-containing groups, and more preferred are divalent silicon-containing groups. Of these, particularly preferred are alkylsilylene, alkylarylsilylene and arylsilylene.

Listed below are examples of the transition metal compounds represented by the above formula [I].

rac-Dimethylsilylene-bis(2,7-dimethyl-4-ethyl-1-indenyl) zirconium dichloride, rac-Dimethylsilylene-bis(2,7-dimethyl-4-n-propyl-1-indenyl)zirconium dichloride, rac-Dimethylsilylene-bis(2,7-dimethyl-4-i-propyl-1-indenyl)zirconium dichloride, rac-Dimethylsilylene-bis(2,7-dimethyl-4-n-butyl-1-indenyl) zirconium dichloride, rac-Dimethylsilylene-bis(2,7-dimethyl-4-sec-butyl-1-indenyl)zirconium dichloride, rac-Dimethylsilylene-bis(2,7-dimethyl-4-t-butyl-1-indenyl) zirconium dichloride, rac-Dimethylsilylene-bis(2,7-dimethyl-4-n-pentyl-1-indenyl)zirconium dichloride,
rac-Dimethylsilylene-bis(2,7-dimethyl-4-n-hexyl-1-indenyl)zirconium dichloride,
rac-Dimethylsilylene-bis(2,7-dimethyl-4-cyclohexyl-1-indenyl)zirconium dichloride,
rac-Dimethylsilylene-bis(2,7-dimethyl-4-methylcyclohexyl-1-indenyl)zirconium dichloride,
rac-Dimethylsilylene-bis(2,7-dimethyl-4-phenylethyl-1-indenyl)zirconium dichloride,
rac-Dimethylsilylene-bis(2,7-dimethyl-4-phenyldichloromethyl-1-indenyl)zirconium dichloride,
rac-Dimethylsilylene-bis(2,7-dimethyl-4-chloromethyl-1-indenyl)zirconium dichloride,
rac-Dimethylsilylene-bis(2,7-dimethyl-4-trimethylsilylenemethyl-1-indenyl)zirconium dichloride,
rac-Dimethylsilylene-bis(2,7-dimethyl-4-trimethylsiloxymethyl-1-indenyl)zirconium dichloride,
rac-Diethylsilylene-bis(2,7-dimethyl-4-i-propyl-1-indenyl)zirconium dichloride,
rac-Di(i-propyl)silylene-bis(2,7-dimethyl-4-i-propyl-1-indenyl)zirconium dichloride,
rac-Di(n-butyl)silylene-bis(2,7-dimethyl-4-i-propyl-1-indenyl)zirconium dichloride,
rac-Di(cyclohexyl)silylene-bis(2,7-dimethyl-4-i-propyl-1-indenyl)zirconium dichloride,
rac-Methylphenylsilylene-bis(2,7-dimethyl-4-i-propyl-1-indenyl)zirconium dichloride,
rac-Methylphenylsilylene-bis(2,7-dimethyl-4-t-butyl-1-indenyl)zirconium dichloride,
rac-Diphenylsilylene-bis(2,7-dimethyl-4-t-butyl-1-indenyl) zirconium dichloride,
rac-Diphenylsilylene-bis(2,7-dimethyl-4-i-propyl-1-indenyl)zirconium dichloride,
rac-Diphenylsilylene-bis(2,7-dimethyl-4-ethyl-1-indenyl) zirconium dichloride,
rac-Di(p-tolyl)silylene-bis(2,7-dimethyl-4-i-propyl-1-indenyl)zirconium dichloride,
rac-Di(p-chlorophenyl)silylene-bis(2,7-dimethyl-4-i-propyl-1-indenyl)zirconium dichloride,
rac-Dimethylsilylene-bis(2-methyl-4-i-propyl-7-ethyl-1-indenyl)zirconium dibromide,
rac-Dimethylsilylene-bis(2,7-dimethyl-4-i-propyl-1-indenyl)zirconium dimethyl,
rac-Dimethylsilylene-bis(2,7-dimethyl-4-i-propyl-1-indenyl)zirconium methylchloride,
rac-Dimethylsilylene-bis(2,7-dimethyl-4-i-propyl-1-indenyl)zirconium-bis(trifluoromethanesulfonato),
rac-Dimethylsilylene-bis(2,7-dimethyl-4-i-propyl-1-indenyl)zirconium-bis(p-phenylsulfinato), and
rac-Dimethylsilylene-bis(2-phenyl-4-i-propyl-7-methyl-1-indenyl)zirconium dichloride.

Of the transition metal compounds represented by the above formula [I], a transition metal compound represented by the following formula [I-a] is particularly preferably used in the invention.

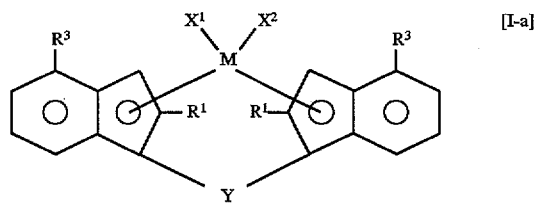

[I-a]

wherein M, $X^1$, $X^2$, $R^1$, $R^3$ and Y are the same as those in the formula [I], and further $R^1$ is preferably hydrogen atom, methyl or an aromatic group.

Listed below are preferred examples of the transition metal compounds represented by the above formula [I-a].
rac-Dimethylsilylene-bis(4-phenyl-1-indenyl)zirconium dichloride,
rac-Dimethylsilylene-bis(2-methyl-4-phenyl-1-indenyl) zirconium dichloride,
rac-Dimethylsilylene-bis(2-methyl-4-(α-naphthyl)-1-indenyl)zirconium dichloride,
rac-Dimethylsilylene-bis(2-methyl-4-(β-naphthyl)-1-indenyl)zirconium dichloride,
rac-Dimethylsilylene-bis(2-methyl-4-(1-anthracenyl)-1-indenyl)zirconium dichloride,
rac-Dimethylsilylene-bis(2-methyl-4-(2-anthracenyl)-1-indenyl)zirconium dichloride,
rac-Dimethylsilylene-bis(2-methyl-4-(9-anthracenyl)-1-indenyl)zirconium dichloride,
rac-Dimethylsilylene-bis(2-methyl-4-(9-phenanthryl)-1-indenyl)zirconium dichloride,
rac-Dimethylsilylene-bis(2-methyl-4-(p-fluorophenyl)-1-indenyl)zirconium dichloride,
rac-Dimethylsilylene-bis(2-methyl-4-(pentafluorophenyl)-1-indenyl)zirconium dichloride,
rac-Dimethylsilylene-bis(2-methyl-4-(p-chlorophenyl)-1-indenyl)zirconium dichloride,
rac-Dimethylsilylene-bis(2-methyl-4-(m-chlorophenyl)-1-indenyl)zirconium dichloride,
rac-Dimethylsilylene-bis(2-methyl-4-(o-chlorophenyl)-1-indenyl)zirconium dichloride,
rac-Dimethylsilylene-bis(2-methyl-4-(o,p-dichlorophenyl)-1-indenyl)zirconium dichloride,
rac-Dimethylsilylene-bis(2-methyl-4-(p-bromophenyl)-1-indenyl)zirconium dichloride,
rac-Dimethylsilylene-bis(2-methyl-4-(p-tolyl)-1-indenyl) zirconium dichloride,
rac-Dimethylsilylene-bis(2-methyl-4-(m-tolyl)-1-indenyl) zirconium dichloride,
rac-Dimethylsilylene-bis(2-methyl-4-(o-tolyl)-1-indenyl) zirconium dichloride,
rac-Dimethylsilylene-bis(2-methyl-4-(o,o'-dimethylphenyl) -1-indenyl)zirconium dichloride,
rac-Dimethylsilylene-bis(2-methyl-4-(p-ethylphenyl)-1-indenyl)zirconium dichloride,
rac-Dimethylsilylene-bis(2-methyl-4-(p-i-propylphenyl)-1-indenyl)zirconium dichloride,
rac-Dimethylsilylene-bis(2-methyl-4-(p-benzylphenyl)-1-indenyl)zirconium dichloride,
rac-Dimethylsilylene-bis(2-methyl-4-(p-biphenyl)-1-indenyl)zirconium dichloride,
rac-Dimethylsilylene-bis(2-methyl-4-(m-biphenyl)-1-indenyl)zirconium dichloride,
rac-Dimethylsilylene-bis(2-methyl-4-(p-trimethylsilylenephenyl)-1-indenyl)zirconium dichloride,
rac-Dimethylsilylene-bis(2-methyl-4-(m-trimethylsilylenephenyl)-1-indenyl)zirconium dichloride,
rac-Dimethylsilylene-bis(2-phenyl-4-phenyl-1-indenyl) zirconium dichloride,
rac-Diethylsilylene-bis(2-methyl-4-phenyl-1-indenyl) zirconium dichloride,
rac-Di(i-propyl)silylene-bis(2-methyl-4-phenyl-1-indenyl) zirconium dichloride,
rac-Di(n-butyl)silylene-bis(2-methyl-4-phenyl-1-indenyl) zirconium dichloride,
rac-Dicyclohexylsilylene-bis(2-methyl-4-phenyl-1-indenyl) zirconium dichloride,
rac-Methylphenylsilylene-bis(2-methyl-4-phenyl-1-indenyl)zirconium dichloride,
rac-Diphenylsilylene-bis(2-methyl-4-phenyl-1-indenyl) zirconium dichloride, rac-Di(p-tolyl)silylene-bis(2-methyl-4-phenyl-1-indenyl) zirconium dichloride,
rac-Di(p-chlorophenyl)silylene-bis(2-methyl-4-phenyl-1-indenyl)zirconium dichloride,
rac-Methylene-bis(2-methyl-4-phenyl-1-indenyl)zirconium dichloride,
rac-Ethylene-bis(2-methyl-4-phenyl-1-indenyl)zirconium dichloride,
rac-Dimethylgermylene-bis(2-methyl-4-phenyl-1-indenyl) zirconium dichloride,
rac-Dimethylstannylene-bis(2-methyl-4-phenyl-1-indenyl) zirconium dichloride,
rac-Dimethylsilylene-bis(2-methyl-4-phenyl-1-indenyl) zirconium dibromide,
rac-Dimethylsilylene-bis(2-methyl-4-phenyl-1-indenyl) zirconium dimethyl,
rac-Dimethylsilylene-bis(2-methyl-4-phenyl-1-indenyl) zirconium methylchloride,
rac-Dimethylsilylene-bis(2-methyl-4-phenyl-1-indenyl) zirconium chloride $SO_2Me$,
rac-Dimethylsilylene-bis(2-methyl-4-phenyl-1-indenyl) zirconium chloride $OSO_2Me$,
rac-Dimethylsilylene-bis(2-methyl-4-phenyl-1-indenyl) titanium dichloride, and
rac-Dimethylsilylene-bis(2-methyl-4-phenyl-1-indenyl) hafnium dichloride.

Of the above compounds, particularly preferred are compounds of the formula [I-a] wherein $R^1$ is methyl.

Also preferably used are transition metal compounds of the formula [I-a] wherein $R^1$ is a hydrocarbon group of 2 to 6 carbon atoms and $R^3$ is an aryl group of 6 to 16 carbon atoms. Examples of such compounds are listed below.

rac-Dimethylsilylene-bis{1-(2-ethyl-4-phenylindenyl) }zirconium dichloride,
rac-Dimethylsilylene-bis{1-(2-ethyl-4-(α-naphthyl) indenyl)}zirconium dichloride,
rac-Dimethylsilylene-bis{1-(2-ethyl-4-(β-naphthyl) indenyl}zirconium dichloride,
rac-Dimethylsilylene-bis{1-(2-ethyl-4-(2-methyl-1-naphthyl)indenyl}zirconium dichloride,
rac-Dimethylsilylene-bis{1-(2-ethyl-4-(5-acenaphthyl) indenyl)}zirconium dichloride,
rac-Dimethylsilylene-bis{1-(2-ethyl-4-(9-anthracenyl) indenyl)}zirconium dichloride,
rac-Dimethylsilylene-bis{1-(2-ethyl-4-(9-phenanthryl) indenyl)}zirconium dichloride,
rac-Dimethylsilylene-bis{1-(2-ethyl-4-(o-methylphenyl) indenyl)}zirconium dichloride,
rac-Dimethylsilylene-bis{1-(2-ethyl-4-(m-methylphenyl) indenyl)}zirconium dichloride,
rac-Dimethylsilylene-bis{1-(2-ethyl-4-(p-methylphenyl) indenyl)}zirconium dichloride,
rac-Dimethylsilylene-bis{1-(2-ethyl-4-(2,3-dimethylphenyl)indenyl)}zirconium dichloride,
rac-Dimethylsilylene-bis{1-(2-ethyl-4-(2,4-dimethylphenyl)indenyl)}zirconium dichloride,
rac-Dimethylsilylene-bis{1-(2-ethyl-4-(2,5-dimethylphenyl)indenyl)}zirconium dichloride,
rac-Dimethylsilylene-bis{1-(2-ethyl-4-(2,4,6-trimethylphenyl)indenyl)}zirconium dichloride,
rac-Dimethylsilylene-bis{1-(2-ethyl-4-(o-chlorophenyl) indenyl)}zirconium dichloride,
rac-Dimethylsilylene-bis{1-(2-ethyl-4-(m-chlorophenyl) indenyl)}zirconium dichloride,
rac-Dimethylsilylene-bis{1-(2-ethyl-4-(p-chlorophenyl) indenyl)}zirconium dichloride,
rac-Dimethylsilylene-bis{1-(2-ethyl-4-(2,3-dichlorophenyl) indenyl)}zirconium dichloride,
rac-Dimethylsilylene-bis{1-(2-ethyl-4-(2,6-dichlorophenyl) indenyl)}zirconium dichloride,
rac-Dimethylsilylene-bis{1-(2-ethyl-4-(3,5-dichlorophenyl) indenyl)}zirconium dichloride,
rac-Dimethylsilylene-bis{1-(2-ethyl-4-(2-bromophenyl) indenyl)}zirconium dichloride,
rac-Dimethylsilylene-bis{1-(2-ethyl-4-(3-bromophenyl) indenyl)}zirconium dichloride,
rac-Dimethylsilylene-bis{1-(2-ethyl-4-(4-bromophenyl) indenyl)}zirconium dichloride,
rac-Dimethylsilylene-bis{1-(2-ethyl-4-(4-biphenylyl) indenyl)}zirconium dichloride,
rac-Dimethylsilylene-bis{1-(2-ethyl-4-(4-trimethylsilylenephenyl)indenyl)}zirconium dichloride,
rac-Dimethylsilylene-bis{1-(2-n-propyl-4-phenylindenyl) }zirconium dichloride,
rac-Dimethylsilylene-bis{1-(2-n-propyl-4-(α-naphthyl) indenyl)}zirconium dichloride,
rac-Dimethylsilylene-biS{1-(2-n-propyl-4-(β-naphthyl) indenyl)}zirconium dichloride,
rac-Dimethylsilylene-bis{1-(2-n-propyl-4-(2-methyl-1-naphthyl)indenyl)}zirconium dichloride,
rac-Dimethylsilylene-bis{1-(2-n-propyl-4-(5-acenaphthyl) indenyl)}zirconium dichloride,
rac-Dimethylsilylene-bis{1-(2-n-propyl-4-(9-anthracenyl) indenyl)}zirconium dichloride,
rac-Dimethylsilylene-bis{1-(2-n-propyl-4-(9-phenanthryl) indenyl)}zirconium dichloride,
rac-Dimethylsilylene-bis{1-(2-i-propyl-4-phenylindenyl) }zirconium dichloride,
rac-Dimethylsilylene-bis{1-(2-i-propyl-4-(α-naphthyl) indenyl)}zirconium dichloride,
rac-Dimethylsilylene-bis{1-(2-i-propyl-4-(β-naphthyl) indenyl)}zirconium dichloride,
rac-Dimethylsilylene-bis{1-(2-i-propyl-4-(2-methyl-1-naphthyl)indenyl)}zirconium dichloride,
rac-Dimethylsilylene-bis{1-(2-i-propyl-4-(5-acenaphthyl) indenyl)}zirconium dichloride,
rac-Dimethylsilylene-bis{1-(2-i-propyl-4-(9-anthracenyl) indenyl)}zirconium dichloride,
rac-Dimethylsilylene-bis{1-(2-i-propyl-4-(9-phenanthryl) indenyl)}zirconium dichloride,
rac-Dimethylsilylene-bis{1-(2-s-butyl-4-phenylindenyl) }zirconium dichloride,
rac-Dimethylsilylene-bis{1-(2-s-butyl-4-(α-naphthyl) indenyl)}zirconium dichloride,
rac-Dimethylsilylene-bis{1-(2-s-butyl-4-(β-naphthyl) indenyl)}zirconium dichloride,
rac-Dimethylsilylene-bis{1-(2-s-butyl-4-(8-methyl-9-naphthyl)indenyl)}zirconium dichloride,
rac-Dimethylsilylene-bis{1-(2-s-butyl-4-(5-acenaphthyl) indenyl)}zirconium dichloride,
rac-Dimethylsilylene-bis{1-(2-s-butyl-4-(9-anthracenyl) indenyl)}zirconium dichloride,
rac-Dimethylsilylene-bis{1-(2-s-butyl-4-(9-phenanthryl) indenyl)}zirconium dichloride,
rac-Dimethylsilylene-bis{1-(2-n-pentyl-4-20 phenylindenyl)}zirconium dichloride,
rac-Dimethylsilylene-bis{1-(2-n-pentyl-4-(α-naphthyl) indenyl)}zirconium dichloride,
rac-Dimethylsilylene-bis{1-(2-n-butyl-4-phenylindenyl) }zirconium dichloride,
rac-Dimethylsilylene-bis{1-(2-n-butyl-4-(α-naphthyl) indenyl)}zirconium dichloride,
rac-Dimethylsilylene-bis{1-(2-n-butyl-4-(β-naphthyl) indenyl)}zirconium dichloride,
rac-Dimethylsilylene-bis{1-(2-n-butyl-4-(2-methyl-1-naphthyl)indenyl)}zirconium dichloride, rac-Dimethylsilylene-bis{1-(2-n-butyl-4-(5-acenaphthyl) indenyl)}zirconium dichloride,
rac-Dimethylsilylene-bis{1-(2-n-butyl-4-(9-anthracenyl) indenyl)}zirconium dichloride,
rac-Dimethylsilylene-bis{1-(2-n-butyl-4-(9-phenanthryl) indenyl)}zirconium dichloride,
rac-Dimethylsilylene-bis{1-(2-i-butyl-4-phenylindenyl)}zirconium dichloride,
rac-Dimethylsilylene-bis{1-(2-i-butyl-4-(α-naphthyl) indenyl)}zirconium dichloride,
rac-Dimethylsilylene-bis{1-(2-i-butyl-4-(β-naphthyl) indenyl)}zirconium dichloride,
rac-Dimethylsilylene-bis{1-(2-i-butyl-4-(2-methyl-1-naphthyl)indenyl)}zirconium dichloride,
rac-Dimethylsilylene-bis{1-(2-i-butyl-4-(5-acenaphthyl) indenyl)}zirconium dichloride,
rac-Dimethylsilylene-bis{1-(2-i-butyl-4-(9-anthracenyl) indenyl)}zirconium dichloride,
rac-Dimethylsilylene-bis{1-(2-i-butyl-4-(9-phenanthryl) indenyl)}zirconium dichloride,
rac-Dimethylsilylene-bis{1-(2-neopentyl-4-phenylindenyl)}zirconium dichloride,
rac-Dimethylsilylene-bis{1-(2-neopentyl-4-(α-naphthyl) indenyl)}zirconium dichloride,
rac-Dimethylsilylene-bis{1-(2-n-hexyl-4-phenylindenyl)}zirconium dichloride,
rac-Dimethylsilylene-bis{1-(2-n-hexyl-4-(α-naphthyl) indenyl)}zirconium dichloride,
rac-Methylphenylsilylene-bis{1-(2-ethyl-4-phenylindenyl)}zirconium dichloride,
rac-Methylphenylsilylene-bis{1-(2-ethyl-4-(α-naphthyl) indenyl)}zirconium dichloride,
rac-Methylphenylsilylene-bis{1-(2-ethyl-4-(9-anthracenyl) indenyl)}zirconium dichloride,
rac-Methylphenylsilylene-bis{1-(2-ethyl-4-(9-phenanthryl) indenyl)}zirconium dichloride,
rac-Diphenylsilylene-bis{1-(2-ethyl-4-phenylindenyl)}zirconium dichloride,
rac-Diphenylsilylene-bis{1-(2-ethyl-4-(α-naphthyl)indenyl)}zirconium dichloride,
rac-Diphenylsilylene-bis{1-(2-ethyl-4-(9-anthracenyl) indenyl)}zirconium dichloride,
rac-Diphenylsilylene-bis{1-(2-ethyl-4-(9-phenanthryl) indenyl)}zirconium dichloride,
rac-Diphenylsilylene-bis{1-(2-ethyl-4-(4-biphenylyl) indenyl)}zirconium dichloride,
rac-Methylene-bis{1-(2-ethyl-4-phenylindenyl)}zirconium dichloride,
rac-Methylene-bis{1-(2-ethyl-4-(α-naphthyl)indenyl)}zirconium dichloride,
rac-Ethylene-bis{1-(2-ethyl-4-phenylindenyl}zirconium dichloride,
rac-Ethylene-bis{1-(2-ethyl-4-(α-naphthyl)indenyl)}zirconium dichloride,
rac-Ethylene-bis{1-(2-n-propyl-4-(α-naphthyl)indenyl)}zirconium dichloride,
rac-Dimethylgermylene-bis{1-(2-ethyl-4-phenylindenyl)}zirconium dichloride,
rac-Dimethylgermylene-bis{1-(2-ethyl-4-(α-naphthyl) indenyl)}zirconium dichloride,
rac-Dimethylgermylene-bis{1-(2-n-propyl-4-phenylindenyl)}zirconium dichloride,
rac-Dimethylstannylene-bis{1-(2-ethyl-4-phenylindenyl)}zirconium dichloride,
rac-Dimethylstannylene-bis{1-(2-ethyl-4-(α-naphthyl) indenyl)}zirconium dichloride,
rac-Dimethylstannylene-bis{1-(2-n-ethyl-4-(9-phenanthryl) indenyl)}zirconium dichloride, and
rac-Dimethylstannylene-bis{1-(2-n-propyl-4-phenylindenyl)}zirconium dichloride.

In the present invention, also employable are transition metal compounds obtained by replacing zirconium metal with metals of titanium, hafnium, vanadium, niobium, tantalum, chromium, molybdenum and tungsten in the above-exemplified compounds.

The transition metal compound is generally used as the olefin polymerization catalyst component in the form of racemic modification, and it can be used either in the form of R type or S type.

The transition metal compound used for the invention can be prepared in accordance with "Journal of Organometallic Chem.", 288 (1985), pp. 63–67 and European Patent Application No. 0,320,762. For example, the compound of the formula [I-a] can be prepared by the following process.

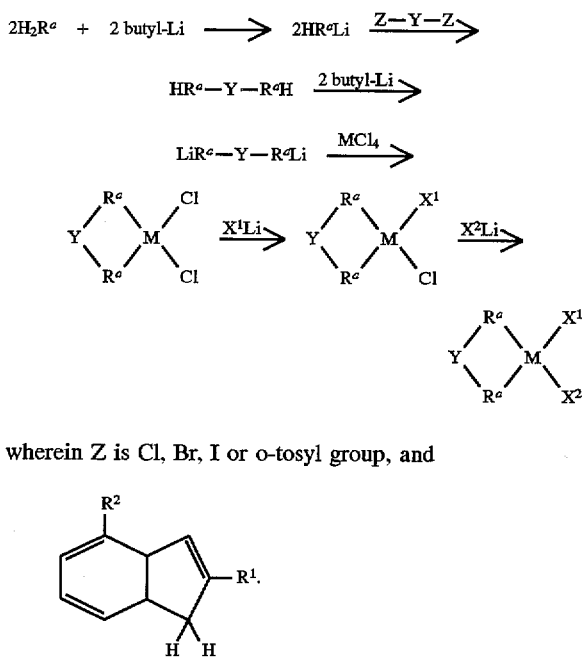

wherein Z is Cl, Br, I or o-tosyl group, and

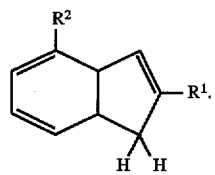

The organoaluminum oxy-compound [B-1] (hereinafter sometimes referred to as "component [B-1]") for forming the olefin polymerization catalyst used for the invention may be either aluminoxane conventionally known or such a benzene-insoluble organoaluminum oxy-compound as exemplified in Japanese Patent Laid-Open Publication No. 78687/1990.

The conventionally known aluminoxane can be prepared by, for example, the following procedures.

(1) A procedure of adding an organoaluminum compound, e.g., trialkylaluminum, to a hydrocarbon medium suspension of compounds containing adsorbed water or salts containing water of crystallization, e.g., magnesium chloride hydrate, copper sulfate hydrate, aluminum sulfate hydrate, nickel sulfate hydrate and cerous chloride hydrate, so as to allow the organoaluminum compound to react with the adsorbed water or the water of crystallization.

(2) A procedure of allowing water, ice or water vapor to directly act on an organoaluminum compound, e.g., trialkylaluminum, in a medium such as benzene, toluene, ethyl ether or tetrahydrofuran.

(3) A procedure of allowing organotin oxide such as dimethyltin oxide or dibutyltin oxide to react with an organoaluminum compound, e.g., trialkylaluminum, in a medium such as decane, benzene or toluene.

The aluminoxane may contain a small amount of an organometallic component. Further, it is possible that the solvent or the unreacted organoaluminum compound is distilled off from the solution after recovery of aluminoxane and the residue is redissolved in a solvent or suspended in a poor solvent for aluminoxane.

Examples of the organoaluminum compounds used for preparing aluminoxane include:

trialkylaluminums, such as trimethylaluminum, triethylaluminum, tripropylaluminum, triisopropylaluminum, tri-n-butylaluminum, triisobutylaluminum, tri-secbutylaluminum, tri-tert-butylaluminum, tripentylaluminum, trihexylaluminum, trioctylaluminum and tridecylaluminum;

tricycloalkylaluminums, such as tricyclohexylaluminum and tricyclooctylaluminum;

dialkylaluminum halides, such as dimethylaluminum chloride, diethylaluminum chloride, diethylaluminum bromide and diisobutylaluminum chloride;

dialkylaluminum hydrides, such as diethylahydride hydride and diisobutylaluminum hydride;

dialkylaluminum alkoxides, such as dimethylaluminum methoxide and diethylaluminum ethoxide; and dialkylaluminum aryloxides, such as diethylaluminum phenoxide.

Of these, preferred are trialkylaluminums and tricycloalkylaluminums, and particularly preferred is trimethylaluminum.

Also employable as the organoaluminum compound used for preparing aluminoxane is isoprenylaluminum represented by the following formula [II]:

$(iC_4H_9)_xAl_y(C_5H_{10})_z$ [II]

wherein x, y and z are each a positive number, and $z \geq 2x$.

The organoaluminum compounds mentioned above are used singly or in combination.

Examples of the solvents used for preparing aluminoxane include aromatic hydrocarbons, such as benzene, toluene, xylene, cumene and cymene; aliphatic hydrocarbons, such as pentane, hexane, heptane, octane, decane, dodecane, hexadecane and octadecane; alicyclic hydrocarbons, such as cyclopentane, cyclohexane, cyclooctane and methylcyclopentane; petroleum fractions, such as gasoline, kerosine and gas oil; and halides of these aromatic, aliphatic and alicyclic hydrocarbons, particularly chlorides and bromides thereof. Also employable are ethers such as ethyl ether and tetrahydrofuran. Of the solvents, preferred are aromatic hydrocarbons and aliphatic hydrocarbons.

The compound [B-2] which reacts with the transition metal compound [A] to form an ion pair (hereinafter sometimes referred to as "component [B-2]"), that is used for forming the olefin polymerization catalyst used for the invention, includes Lewis acid, ionic compounds and carborane compounds, as described in Japanese Patent Laid-Open Publications No. 501950/1989, No. 502036/1989, No. 179005/1991, No. 179006/1991, No. 207703/1991 and No. 207704/1991, and U.S. Pat. No. 547,718.

Examples of the Lewis acid include triphenylboron, tris(4-fluorophenyl)boron, tris(p-tolyl)boron, tris(o-tolyl)boron, tris(3,5-dimethylphenyl)boron, tris(pentafluorophenyl)boron, $MgCl_2$, $Al_2O_3$ and $SiO_2$—$Al_2O_3$.

Examples of the ionic compounds include triphenylcarbeniumtetrakis(pentafluorophenyl)borate, tri-n-butylammoniumtetrakis(pentafluorophenyl)borate, N,N-dimethylaniliniumtetrakis(pentafluorophenyl)borate and ferroceniumtetrakis(pentafluorophenyl)borate.

Examples of the carborane compounds include dodecaborane, 1-carbaundecaborane, bis-n-butylammonium (1-carbedodeca)borate, tri-n-butylammonium(7,8-dicarbaundeca)borate and tri-n-butylammonium (tridecahydride-7-carbaundeca)borate.

The compounds [B-2] which react with the transition metal compound [A] to form an ion pair can be used in combination of two or more kinds.

The organoaluminum compound [C] (hereinafter sometimes referred to as "component [C]") for forming the olefin polymerization catalyst used for the invention is, for example, an organoaluminum compound represented by the following formula [III]:

$R^9{}_nAlX_{3-n}$ [III]

wherein $R^9$ is a hydrocarbon group of 1 to 12 carbon atoms, X is a halogen atom or a hydrogen atom, and n is 1 to 3.

In the above formula [III], $R^9$ is a hydrocarbon group of 1 to 12 carbon atoms, for example, an alkyl group, a cycloalkyl group or an aryl group. Particular examples thereof include methyl, ethyl, n-propyl, isopropyl, isobutyl, pentyl, hexyl, octyl, cyclopentyl, cyclohexyl, phenyl and tolyl.

Examples of such organoaluminum compound [C] include:

trialkylaluminums, such as trimethylaluminum, triethylaluminum, triisopropylaluminum, triisobutylaluminum, trioctylaluminum, tri(2-ethylhexyl) aluminum and tridecylaluminum;

alkenylaluminums, such as isoprenylaluminum;

dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichoride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylaluminum dichloride and ethylaluminum dibromide; and alkylaluminum hydrides, such as diethylaluminum hydride and diisobutylaluminum hydride.

Also employable as the organoaluminum compound [C] is a compound represented by the following formula [IV]:

$R^9{}_nAlL_{3-n}$ [IV]

wherein $R^9$ is the same as above; L is —$OR^{10}$ group, —$OSiR^{11}{}_3$ group, —$OAlR^{12}{}_2$ group, —$NR^{13}{}_2$ group, —$SiR^{14}{}_3$ group or —$N(R^{15})AlR^{16}{}_2$ group; n is 1 to 2; $R^{10}$, $R^{11}$, $R^{12}$ and $R^{16}$ are each methyl, ethyl, isopropyl, isobutyl, cyclohexyl, phenyl or the like, $R^{13}$ is hydrogen, methyl, ethyl, isopropyl, phenyl, trimethylsilylene or the like; and $R^{14}$ and $R^{15}$ are each methyl, ethyl or the like.

Of such organoaluminum compounds, preferred are compounds of $R^7{}_nAl(OAlR^{10}{}_2)_{3-n}$, for example, $Et_2AlOAlEt_2$ and $(iso\text{-}Bu)_2AlOAl(iso\text{-}Bu)_2$.

Of the organoaluminum compounds represented by the formulas [III] and [IV], preferred are compounds of the formula $R^7{}_3Al$, and particularly preferred are compounds of said formula wherein $R^7$ is an isoalkyl group.

The olefin polymerization catalyst used for the invention can be prepared by mixing the component [A] and the component [B-1] (or the component [B-2]), and if desired, the component [C] in an inert hydrocarbon solvent or an olefin solvent.

Examples of the inert hydrocarbon solvents used for preparing the olefin polymerization catalyst include aliphatic hydrocarbons, such as propane, butane, pentane, hexane, heptane, octane, decane, dodecane and kerosine; alicyclic hydrocarbons, such as cyclopentane, cyclohexane and methylcyclopentane; aromatic hydrocarbons, such as benzene, toluene and xylene; halogenated hydrocarbons, such as ethylene chloride, chlorobenzene and dichloromethane; and mixtures of these hydrocarbons.

The order of mixing the above components may be arbitrarily determined, but preferred is:

mixing the component [B-1] (or the component [B-2]) with the component [A];

mixing first the component [B-1] with the component [C] and then with the component [A];

mixing first the component [A] with the component [B-1] (or the component [B-2]) and then with the component [C]; or mixing first the component [A] with the component [C] and then with the component [B-1] (or the component [B-2]).

In the mixing of the above components, an atomic ratio of aluminum in the component [B-1] to the transition metal iN the transition metal compound [A], (Al/transition metal), is in the range of usually 10 to 10,000, preferably 20 to 5,000, and a concentration of the component [A] is in the range of about $10^{-8}$ to $10^{-1}$ mol/liter, preferably $10^7$ to $5 \times 10^{-2}$ mol/liter.

When the component [B-2] is used, a molar ratio of the component [A] to the component [B-2], (component [A]/component [B-2]), is in the range of usually 0.01 to 10, preferably 0.1 to 5, and a concentration of the component [A] is in the range of about $10^{-8}$ to $10^{-1}$ mol/liter, preferably $10^{-7}$ to $5 \times 10^{-2}$ mol/liter.

When the component [C] is used, an atomic ratio of the aluminum atom ($Al_c$) in the component [C] to the aluminum atom ($Al_{B-1}$) in the component [B-1], ($Al_c/Al_{B-1}$), is in the range of usually 0.02 to 20, preferably 0.2 to 10.

The above-mentioned catalyst components may be mixed in a polymerizer, or a mixture of the components preliminarily prepared may be added to a polymerizer.

If the components are preliminarily mixed, the mixing temperature is in the range of usually $-50°$ to $150°$ C., preferably $-20°$ to $120°$ C.; and the contact time is in the range of 1 to 1,000 minutes, preferably 5 to 600 minutes. The mixing temperature may be varied during the mixing procedure.

The olefin polymerization catalyst used for the invention may be a solid olefin polymerization catalyst in which at least one of the above components [A], [B] and [C] is supported on an inorganic or organic, granular or particulate solid carrier.

The inorganic carrier is preferably a porous oxide, and examples thereof include $SiO_2$ and $Al_2O_3$.

Examples of the granular or particulate solid organic compounds include polymers and copolymers produced by using α-Olefins (e.g., ethylene, propylene and 1-butene) or styrene, as major component.

The olefin polymerization catalyst used for the invention may be an olefin polymerization catalyst formed from the above-mentioned fine particle carrier, the component [A], the component [B] and an olefin polymer produced by prepolymerization, and if desired, the component [C].

In the prepolymerization, olefins, such as propylene, ethylene and 1-butene, can be employed. Also employable are mixtures of these olefins and other olefins.

In addition to the above components, the olefin polymerization catalyst used for the invention may further contain other components useful for the olefin polymerization, for example, water as a catalyst component.

The propylene elastomer of the invention can be prepared by copolymerizing propylene and 1-butene in the presence of the above-mentioned olefin polymerization catalyst in such a manner that the aforesaid monomer composition would be finally obtained.

The polymerization can be carried out by any of a liquid phase polymerization process (e.g., suspension polymerization process, solution polymerization process) and a gas phase polymerization process.

In the liquid phase polymerization process, the same inert hydrocarbon solvent as used for preparing the catalyst previously mentioned can be employed, or propylene is also employable as a solvent.

In the suspension polymerization process, the polymerization temperature is desired to be in the range of usually $-50°$ to $100°$ C., preferably $0°$ to $90°$ C., and in the solution polymerization process, the temperature is desired to be in the range of usually $0°$ to $250°$ C., preferably $20°$ to $200°$ C. In the gas phase polymerization process, the temperature is desired to be in the range of usually $0°$ to $120°$ C., preferably $20°$ to $100°$ C.

The polymerization pressure is in the range of usually atmospheric pressure to 100 kg/cm$^2$, preferably atmospheric pressure to 50 kg/cm$^2$. The polymerization reaction can be carried out either batchwise, semicontinuously or continuously.

The polymerization can be carried out in two or more stages having different reaction conditions.

The molecular weight of the resulting propylene elastomer can be regulated by allowing hydrogen to exist in the polymerization system or varying the polymerization temperature or the polymerization pressure.

EFFECT OF THE INVENTION

The propylene elastomer according to the invention has a high triad tacticity, and is excellent in rigidity, heat resistance, scratch resistance, transparency, heat sealing properties and blocking resistance. Therefore, it can be favorably used for sheets, films, etc., and particularly favorably used as a sealant.

Especially in the case of a film containing the propylene elastomer of the invention, its heat-sealing temperature does not change with time even after the film is stored for a long period of time, and hence stable heat sealing can be ensured.

Further, the propylene elastomer of the invention has a lower melting point than conventional elastomers provided that they are the same in the ratio between propylene and 1-butene, and therefore the heat-sealing temperature can be lowered. Moreover, molded articles produced from the propylene elastomer of the invention have high surface hardness, and hence they are hardly scratched.

EXAMPLE

The present invention will be further described with reference to the following examples, but it should be construed that the invention is in no way limited to those examples.

Measurement of properties

[1-Butene content]

The 1-butene content was determined using $^{13}$C-NMR.

[Intrinsic viscosity [η]]

The intrinsic viscosity [η] was measured in Decalin (decahydrophthalene) at $135°$ C. and expressed by dl/g.

[Molecular weight distribution (Mw/Mn)]

The molecular weight distribution (Mw/Mn) was measured in the following manner using GPC-150C produced by Millipore Co.

A separatory column of TSK-GNH-Ht having a diameter of 27 mm and a length of 600 mm was used, and the column temperature was set to 140° C. A sample (concentration: 0.1% by weight, amount: 500 microliters) was moved in the column at a rate of 1.0 ml/min using o-dichlorobenzene (available from Wako Junyaku Kogyo K.K.) as a mobile phase and 0.025% by weight of BHT (available from Takeda Chemical Industries, Ltd.) as an antioxidant. A differential refractometer was used as a detector. With regard to standard polystyrenes, polystyrenes available from Toso Co., Ltd. were used as those of Mw<1,000 and Mw>4×10$^6$, and polystyrenes available from Pressure Chemical Co. were used as those of 1,000<Mw<4×10$^6$.

[B value]

The B value (monomer distribution) was determined as follows. A $^{13}$C-NMR spectrum of a sample obtained by homogeneously dissolving about 200 mg of a copolymer in 1 ml of hexachlorobutadiene in a sample tube having a diameter of 10 mm was measured under the measuring conditions of usually a temperature of 120° C., a measuring frequency of 25.05 MHz, a spectral width of 1,500 Hz, a filter width of 1,500 Hz, pulse repetition time of 4.2 sec and integrating times of 2,000 to 5,000. From the spectrum obtained, $P_E$, $P_O$ and $P_{EO}$ were sought, and the B value was calculated using $P_E$, $P_O$ and $P_{EO}$.

[Triad tacticity]

A $^{13}$C-NMR spectrum of a hexachlorobutadiene solution of a sample (based on tetramethylsilane) was measured, and a proportion (%) of the area of the peaks shown in the region of 21.0 to 21.9 ppm to the total area (100%) of the peaks shown in the region of 19.5 to 21.9 ppm was calculated.

[Proportion of inversion bonds based on 2,1-insertions]

The proportion of inversion bonds based on 2,1-insertions was determined in the aforesaid manner using the $^{13}$C-NMR spectrum with reference to "Polymer", 30, 1350 (1989).

[Melting point (Tm)]

The melting point (Tm) was determined from an endothermic curve which was obtained by heating about 5 mg of a sample charged in an aluminum pan to 200° C. at a rate of 10° C./min, keeping it at 200° C. for 5 minutes, then cooling it to room temperature at a rate of 20° C./min and finally heating it at a rate of 10° C./min. The measurement was conducted using a DSC-7 type measuring device manufactured by Perkin Elmer Co.

[Crystallinity]

The crystallinity was determined by subjecting a press sheet having a thickness of 1.0 mm to X-ray diffractometry after at least 24 hours had passed since the molding procedure.

[Heat-sealing starting temperature]

(1) Preparation of film

On a press plate, an aluminum sheet having a thickness of 0.1 mm, a PET sheet and an aluminum sheet having a thickness of 100 μm from which a central portion of 15 cm×15 cm had been cut away were superposed in this order, and 3.3 g of a sample was put on the center (cut portion) of the aluminum sheet. Then, a PET sheet, an aluminum plate and a press plate were further superposed thereon.

The sample thus interposed between the press plates was put in a hot press apparatus at 200° C. and preheated for about 7 minutes. Operations of applying pressure (50 kg/cm$^2$-G) and releasing pressure were repeated several times to remove air bubbles in the sample. Finally, the pressure was raised to 100 kg/cm$^2$-G, and the sample was heated for 2 minutes under the same pressure. After releasing of pressure, the press plates with the sample were taken out of the pressing machine and transferred into other pressing machine kept at 0° C. at the pressing portion. Then, the sample was cooled for 4 minutes under a pressure of 100 kg/cm$^2$-G. The pressure was released, and the sample was taken out. Thus, a film having a thickness of about 150 to 170 μm was obtained, and the film was used for measuring the heat-sealing strength.

(2) Measurement of heat-sealing strength

The film was cut into strips having a width of 15 mm. Two of the strips were superposed one upon another, and they were interposed between two Teflon sheets each having a thickness of 0.1 mm, followed by heat sealing. The heat sealing was carried out by properly varying the temperature of the hot plate upper portion by 5° C. while keeping the temperature of the lower portion constant at 70° C. The heat-sealing pressure was 2 kg/cm$^2$-G, the heat-sealing time was 1 second, and the seal width was 5 mm (seal area: 15 mm ×5 mm).

The heat-sealing strength was determined by subjecting the film, which had undergone the heat sealing at the above-mentioned heat-sealing temperatures, to a tensile test at a tensile rate of 30 cm/min so as to measure peel strength.

The peel strength of the film was measured at each of the heat-sealing temperatures (variations by every 5° C.) in the above-mentioned manner, and the heat-sealing temperatures and the peel strength were plotted to give a curve. From this curve, a heat-sealing temperature corresponding to the peel strength of 300 g/15 cm was read, and this temperature was regarded as the heat-sealing starting temperature.

(3) Measurement of heat-sealing strength after aging

The film was aged by placing the film in a constant temperature bath at 50° C. for 7 days. In the aging, paper was laid on both surfaces of the film so that the films were not brought into contact with each other. The film having been subjected to the aging was measured on the heat-sealing starting temperature in the manner described above.

[Martens hardness]

The Martens hardness was measured as follows. A surface of a press sheet of 1 mm was scratched with a diamond plumb using a Martens scratch tester (manufactured by Tokyo Shoki K.K.) with applying a given load (5 g) to the plumb, and the scratch mark on the surface was measured. The width of the scratch mark on the specimen thus tested was measured by a microscope, and a reciprocal (mm$^{-1}$) of the obtained value was regarded as the Martens hardness.

[Blocking stress]

The blocking stress was evaluated in accordance with ASTM D1893. That is, two of films each having a width of 10 cm and a length of 15 cm were superposed one upon another, and they were interposed between two glass plates. The films with the glass plates were allowed to stand in an air oven at 50° C. with applying a load of 10 kg to the films (sample). After 7 days, the sample was taken out, and the peel strength was measured. The peel strength per 1 cm was taken as a value of the blocking strength.

[Haze]

The haze was measured in accordance with ASTM D1003-61 using the film prepared for measuring the heat-sealing starting temperature.

Preparation Example

Synthesis of rac-dimethylsilylene-bis{(1-(2-ethyl-4-phenylindenyl)}zirconium dichloride Synthesis of 3-(2-biphenylyl)-2-ethylpropionic acid To a 500-ml four-necked round flask (equipped with stirrer, Dimroth condenser, dropping funnel and thermometer) were introduced 13.46 g (120 mmol) of potassium t-butoxide, 100 ml of toluene and 20 ml of N-methylpyrrolidone. In a nitrogen atmosphere, to the flask was dropwise added a solution obtained by dissolving 20.7 g (110 mmol) of diethyl ethylmalonate in 50 ml of toluene, with heating to 60° C. After the dropping was completed, the mixture was reacted for 1 hour at the same temperature. Then, to the mixture was dropwise added at the same temperature a solution obtained by dissolving 20.27 g (100 mmol) of 2-phenylbenzyl bromide in 30 ml of toluene. After the dropping was completed, the system was heated and refluxed for 2 hours. The reaction mixture was poured into 200 ml of water, and 2N—HCl was added to adjust pH of the mixture to 1. The organic phase was separated, and the aqueous phase was extracted three times with 100 ml of toluene, followed by mixing the organic phases together. The whole organic phase was washed with a saturated saline solution until the organic phase became neutral, and dried with anhydrous $Na_2SO_4$. Then, the solvent was concentrated under reduced pressure to obtain 36.7 g of an yellow orange liquid concentrate.

To a 1-liter four-necked round flask (equipped with stirrer, Dimroth condenser, dropping funnel and thermometer) were introduced 67.3 g (1.02 mol) of potassium hydroxide and 160 ml of a methanol aqueous solution (methanol/water=4/1 (v/v)). In a nitrogen atmosphere at room temperature, to the flask was dropwise added a solution obtained by dissolving the concentrate obtained above in 50 ml of a methanol aqueous solution (methanol/water=4/1 (v/v)). After the dropping was completed, the system was heated and refluxed for 4 hours. Thereafter, the system was cooled to room temperature, and the solid precipitated was filtered. The solid was then dissolved in water, and to the solution was added sulfuric acid so that the pH of the solution became acidic (pH=1). The solution was extracted five times with 100 ml of methylene chloride, followed by mixing the organic phases together. The whole organic phase was dried with anhydrous $Na_2SO_4$. Then, the solvent was concentrated under reduced pressure to obtain 24.2 g of a white solid product.

Subsequently, to 300-ml three-necked round flask (equipped with stirrer chip, Dimroth condenser and thermometer) were introduced 24.2 g of the white solid obtained above, 56 ml of acetic acid, 37 ml of water and 13.1 ml of concentrated sulfuric acid, and they were refluxed for 6 hours in a nitrogen atmosphere. After the reaction was completed, the acetic acid was distilled off under reduced pressure. To the reaction mixture was added 50 ml of water, and the mixture was extracted three times with 50 ml of methylene chloride, followed by mixing the organic phases together. The whole organic phase was washed with 50 ml of a saturated saline solution and dried with anhydrous $Na_2SO_4$. Then, the solvent was distilled off under reduced pressure, and the residue was separated and purified by silica gel chromatography (developed with hexane/ethyl acetate (2/1→1/1, by volume)) to obtain 13.7 g of a white solid (yield: 54%). The properties of the product thus obtained are described below.

FD-MS: 254 ($M^+$)

m.P.: 91.2°–94.0° C.

NMR ($CDCl_3$, 90 Hz): δ =0.71 (t, J=7.2 Hz, 3H, $CH_3$); 1.16–1.58 (m, 2H); 2.32 (b quin, J=7.0 Hz, 1H,

|
—CH—);

2.61–2.99 (m, 2H); 6.89–7.47 (m, 9H)
IR (KBr disk): 1696 $cm^1$ ($v_{C=O}$)

Synthesis of 3-(2-biphenylyl)-2-ethylpropionyl chloride

To a 100-ml three-necked round flask (equipped with stirrer chip, Dimroth condenser, thermometer and NaOH trap) were introduced 13.3 g (52.4 mmol) of the 3-(2-biphenylyl)-2-ethylpropionic acid and 25.9 ml (355 mmol) of thionyl chloride, and they were refluxed for 2.5 hours with heating in a nitrogen atmosphere. After the reaction was completed, the unreacted thionyl chloride was distilled off under reduced pressure to obtain 15.2 g of a crude product of yellow orange liquid. This acid chloride was used for the next reaction without further purification. The properties of the product thus obtained are described below.

IR (Neat): 1786 $cm^1$ ($v_{C=O}$)

Synthesis of 4-ethyl-2-phenyl-1-indanone

To a 200-ml three-necked round flask (equipped with stirrer chip, Dimroth condenser, dropping funnel, thermometer and NaOH trap) were introduced 8.04 g (60.3 mmol) of anhydrous aluminum chloride and 50 ml of carbon disulfide. Under ice cooling, to the flask was dropwise added a solution obtained by dissolving 15.2 g (52.4 mmol) of the 3-(2-biphenylyl)-2-ethylpropionyl chloride obtained above in 21 ml of carbon disulfide. After the dropping was completed, the internal temperature was elevated to room temperature to perform reaction for 1 hour. Then, the reaction solution was poured into 200 ml of ice water to decompose it and extracted twice with 100 ml of ether, followed by mixing the organic phases together. The whole organic phase was washed with 100 ml of a saturated $NaHCO_3$ aqueous solution and then washed with 100 ml of a saturated saline solution, followed by drying with anhydrous $Na_2SO_4$. The solvent was distilled off under reduced pressure, and the residue was separated and purified by silica gel chromatography (developed with hexane/ethyl acetate (10/1, by volume)) to obtain 10.8 g of the aimed product as an yellow solid (yield: 88%). The properties of the product thus obtained are described below.

NMR ($CDCl_3$, 90 Hz): δ =0.98 (t, J=7.2 Hz, 3H, $CH_3$); 1.60–2.20 (m, 2H); 2.42–2.82 ( m, 1H,

NMR ($CDCl_3$, 90 Hz):
δ = 0.98 (t, J=7.2 Hz, 3H, $CH_3$);
1.60–2.20 (m, 2H);

|
2.42–2.82 (m, 1H, —CH—);

2.80 (dd, J=3.8 Hz, 16.5 Hz, 1H);
3.36 (dd, J=7.6 Hz, 16.5 Hz, 1H);
7.09–7.91 (m, 8H)
IR (Neat): 1705 $cm^{-1}$ ($v_{C=O}$)

2.80 (dd, J=3.8 Hz, 16.5 Hz, 1H); 3.36 (dd, J=7.6 Hz, 16.5 Hz, 1H); 7.09–7.91 (m, 8H)
IR (Neat): 1705 $cm^{-1}$ ($v_{C=O}$)

Synthesis of 2-ethyl-1-hydroxy-4-phenylindan

To a 200-ml three-necked round flask (equipped with stirrer chip, Dimroth condenser, dropping funnel and thermometer) were introduced 0.85 g (22.6 mmol) of sodium boron hydride and 28 ml of ethanol. In a nitrogen atmosphere at room temperature, to the flask was dropwise added a solution obtained by dissolving 10.6 g (45.1 mmol) of the 2-ethyl-4-phenyl-1-indanone obtained above in 20 ml of ethanol. After the dropping was completed, the temperature of the system was elevated to 50° C. so as to further perform reaction for 3.5 hours. After the reaction, the system was cooled, and acetone was dropwise added to decompose the unreacted sodium boron hydride. Then, the reaction mixture was concentrated under reduced pressure and extracted with 50 ml of water and 50 ml of ether. The organic phase was separated, and the aqueous phase was extracted twice with 50 ml of ether, followed by mixing the organic phases together. The whole organic phase was washed with 100 ml of a saturated saline solution and dried with anhydrous $Na_2SO_4$. Then, the solvent was distilled off under reduced pressure to obtain 10.67 g of the aimed product (mixture of two kinds of isomers) as a viscous light yellow liquid (yield: 99%). The properties of the product thus obtained are described below.

NMR ($CDCl_3$, 90 Hz): δ =1.02 (t, J=7.1 Hz, 3H, $CH_3$); 1.31–3.28 (m, 5H); 4.86, 5.03 (each d, each J=6.4 Hz, J=5.1 Hz, together 1H, NMR ($CDCl_3$, 90 Hz):
δ = 1.02 (t, J =7.1 Hz, 3H, $CH_3$);
1.31–3.28 (m, 5H);
4.86, 5.03 (each d, each J=6.4 Hz, J=5.1

Hz, together 1H, —CH—O—);

7.10–7.66 (m, 8H);
IR (Neat): 3340 cm$^{-1}$ ($v_{OH}$)

7.10–7.66 (m, 8H);
IR (Neat): 3340 cm$^{-1}$ ($v_{OH}$)

Synthesis of 2-ethyl-4-phenylindene

To a 300-ml four-necked round flask (equipped with stirrer chip, dropping funnel and thermometer) were introduced 9.78 g (41.3 mmol) of the 2-ethyl-1-hydroxy-4-phenylindan obtained above, 17.2 ml (123.8 mmol) of triethylamine, 0.25 g (2.1 mmol) of 4-dimethylaminopyridine and 98 ml of methylene chloride. In a nitrogen atmosphere under ice cooling, to the flask was dropwise added slowly a solution obtained by dissolving 6.4 ml (82.5 mmol) of methanesulfonyl chloride in 6.5 ml of methylene chloride. After the dropping was completed, the reaction was further performed for 3.5 hours. After the reaction mixture was poured into 250 ml of ice water, the organic phase was separated, and the aqueous phase was extracted twice with 50 ml of methylene chloride, followed by mixing the organic phases together. The whole organic phase was washed with a saturated $NaHCO_3$ aqueous solution and then washed with a saturated saline solution, followed by drying with anhydrous $Na_2SO_4$. The solvent was distilled off under reduced pressure, and the residue was separated and purified by silica gel chromatography (developed with hexane) to obtain 6.56 g of the aimed product (mixture of two kinds of isomers) as a light yellow liquid (yield: 73%) The properties of the product thus obtained are described below.

NMR ($CDCl_3$, 90 MHz): δ =1.20 (t, J=7.6 Hz, 3H, $CH_3$); 2.49 (q, J=7.6 Hz, 2H); 3.41 (s, 2H); 6.61, 6.72 (each bs, together 1H); 7.09–8.01 (m, 8H);

Synthesis of dimethylsilylene-bis(2-ethyl-4-phenylindene)

To a 200-ml three-necked round flask (equipped with stirrer chip, Dimroth condenser, dropping funnel and thermometer) were introduced 5.0 g (22.8 mmol) of the 2-ethyl-4-phenylindene obtained above, 80 mg (0.63 mmol) of copper thiocyanate and 50 ml of anhydrous ether. In a nitrogen atmosphere under ice cooling, to the flask was dropwise added slowly 15.7 ml (25.1 mmol) of a hexane solution of n-butyllithium (concentration: 1.6M). After the dropping was completed, the temperature of the system was elevated to room was elevated to room temperature so as to further perform reaction for 1 hour. Then, to the flask was dropwise added slowly a solution obtained by dissolving 1.52 ml (12.6 mmol) of dimethyldichlorosilane in 4.5 ml of anhydrous ether. After the dropping was completed, the reaction was further performed for 12 hours at room temperature. The reaction mixture was filtered by Celite, and the filtrate was poured into 50 ml of a saturated ammonium chloride aqueous solution. The organic phase was separated, and the aqueous phase was extracted with 50 ml of ether, followed by mixing the organic phases together. The whole organic phase was washed with a saturated saline solution and dried with anhydrous $Na_2SO_4$. Then, the solvent was distilled off under reduced pressure, and the residue was separated by silica gel chromatography (developed with hexane → hexane/methylene chloride (20/1, by volume)) to obtain 4.5 g of the aimed product (mixture of two kinds of isomers) as a light yellow solid (yield: 80%). The properties of the product thus obtained are described below.

NMR ($CDCl_3$, 90 Hz): δ =–0.23, –0.17 (each s, together 6H, Si—$CH_3$); 1.12, 1.19 (each t, each J=7.4 Hz, together 6H, $CH_3$); 2.44 (bq, J=7.4 Hz, 4H); 3.81 (s, 2H, NMR ($CDCl_3$, 90 Hz)
δ = –0.23, –0.17 (each s, together 6H, Si—$CH_3$);
1.12, 1.19 (each t, each J=7.4 Hz, together 6H, $CH_3$);
2.44 (bq, J=7.4 Hz, 4H);

3.81 (s, 2H, —CH—Si—);

6.75 (bs, 2H, 3-H-Ind);
6.88–7.74 (m, 16H);

6.75 (bs, 2H, 3-H-Ind); 6.88–7.74 (m, 16H);

Synthesis of rac-dimethylsilylene-bis{1-(2-ethyl-4-phenylindenyl}zirconium dichloride, To a 50-ml three-necked round flask (equipped with stirrer chip, beads condenser, dropping funnel and thermometer) were introduced 0.84 g (1.69 mmol) of the dimethylsilylene-bis(2-ethyl-4-phenylindene) obtained above and 17 ml of anhydrous ether. At room temperature, to the flask was dropwise added slowly 2.25 ml (3.56 mmol) of a hexane solution of n-butyllithium (concentration: 1.58M). After the dropping was completed, the reaction was further performed for 13.5 hours. The reaction solution was cooled to –70° C. in a dry ice/acetone bath, and to the solution was gradually added 0.395 g (1.69 mmol) of $ZrCl_4$ powder. After the addition was completed, the resulting mixture was allowed to stand overnight with stirring. Then, the solvent was distilled off at room temperature under reduced pressure. After 30 ml of methylene chloride was added, impurities were filtered. The filtrate was concentrated at room temperature to precipitate a solid. The solid precipitated was filtered, washed twice with 3 ml of anhydrous ether and dried under reduced pressure to obtain 0.17 g of the aimed product as an orange yellow solid (yield: 15%). The properties of the product thus obtained are described below.

NMR (CDCl$_3$, 90 MHz): δ =1.09 (t, J=7.3 Hz, 6H, CH$_3$); 1.34 (s, 6H, Si—CH$_3$); 2.46 (quin, J=7.3 Hz, 2H); 2.73 (quin, J=7.3 Hz, 2H); 6.96 (S, 2H, 3-H-Ind); 6.99–7.88 (m, 16H)

Example 1

To a 2-liter autoclave thoroughly purged with nitrogen were introduced 900 ml of hexane and 90 g of 1-butene. To the flask was added 1 mmol of triisobutylaluminum, and the temperature of the system was elevated to 70° C. Then, propylene was fed to the system so that the total pressure became 7 kg/cm$^2$-G. To the system were further added 0.30 mmol of methylaluminoxane and 0.001 mmol (in terms of Zr atom) of rac-dimethylsilylene-bis{1-(2-methyl-4-phenylindenyl)}zirconium dichloride prepared in a manner similar to that of Preparation Example, and polymerization was carried out for 30 minutes while propylene was continuously fed to keep the total pressure at 7 kg/cm$^2$-G. After the polymerization, the system was degassed and a polymer was recovered in a large amount of methanol. The polymer was vacuum dried at 110° C. for 12 hours.

The amount of the polymer (propylene elastomer) obtained was 39.7 g, and the polymerization activity was 79 kg-polymer/mmol-Zr.hr. This polymer contained units derived from 1-butene in amounts of 26.4% by mol, and had an intrinsic viscosity [η] of 1.60 dl/g and a melting point of 88.4° C. The proportion of the inversion bonds based on the 2,1-insertions was about 0.02%.

The properties measured on the polymer are set forth in Table 1.

Example 2

To a 2-liter autoclave thoroughly purged with nitrogen were introduced 900 ml of hexane and 60 g of 1-butene. To the flask was added 1 mmol of triisobutylaluminum, and the temperature of the system was elevated to 70° C. Then, propylene was fed to the system so that the total pressure became 7 kg/cm$^2$-G. To the system were further added 0.30 mmol of methylaluminoxane and 0.001 mmol (in terms of Zr atom) of rac-dimethylsilylene-bis{1-(2-methyl-4-phenylindenyl)}zirconium dichloride prepared in a manner similar to that of Preparation Example, and polymerization was carried out for 30 minutes while propylene was continuously fed to keep the total pressure at 7 kg/cm$^2$-G. After the polymerization, the system was degassed and a polymer was recovered in a large amount of methanol. The polymer was vacuum dried at 110° C. for 12 hours.

The amount of the polymer (propylene elastomer) obtained was 45.2 g, and the polymerization activity was 90 kg-polymer/mmol-Zr.hr. This polymer contained units derived from 1-butene in amounts of 20.2% by mol, and had an intrinsic viscosity [η] of 1.90 dl/g and a melting point of 101.5° C. The proportion of the inversion bonds based on the 2,1-insertions was about 0.02%.

The properties measured on the polymer are set forth in Table 1.

Example 3

To a 2-liter autoclave thoroughly purged with nitrogen were introduced 950 ml of hexane and 30 g of 1-butene. To the flask was added 1 mmol of triisobutylaluminum, and the temperature of the system was elevated to 70° C. Then, propylene was fed to the system so that the total pressure became 7 kg/cm$^2$-G. To the system were further added 0.30 mmol of methylaluminoxane and 0.001 mmol (in terms of Zr atom) of rac-dimethylsilylene-bis{1-(2-methyl-4-phenylindenyl)}zirconium dichloride prepared in a manner similar to that of Preparation Example, and polymerization was carried out for 30 minutes while propylene was continuously fed to keep the total pressure at 7 kg/cm$^2$-G. After the polymerization, the system was degassed and a polymer was recovered in a large amount of methanol. The polymer was vacuum dried at 110° C. for 12 hours.

The amount of the polymer (propylene elastomer) obtained was 52.1 g, and the polymerization activity was 104 kg-polymer/mmol-Zr.hr. This polymer contained units derived from 1-butene in amounts of 13.9% by mol, had an intrinsic viscosity [η] of 2.51 dl/g and a melting point of 116.3° C. The proportion of the inversion bonds based on the 2,1-insertions was about 0.02%.

The properties measured on the polymer are set forth in Table 1.

Comparative Example 1

To a 2-liter autoclave thoroughly purged with nitrogen were introduced 830 ml of hexane and 100 g of 1-butene. To the flask was added 1 mmol of triisobutylaluminum, and the temperature of the system was elevated to 70° C. Then, propylene was fed to the system so that the total pressure became 7 kg/cm$^2$-G. To the system were further added 1 mmol of triethylaluminum and 0.005 mmol (in terms of Ti atom) of a titanium catalyst supported on magnesium chloride, and polymerization was carried out for 30 minutes while propylene was continuously fed to keep the total pressure at 7 kg/cm$^2$-G. After the polymerization, the system was degassed and a polymer was recovered in a large amount of methanol. The polymer was vacuum dried at 110° C. for 12 hours.

The amount of the polymer obtained was 33.7 g, and the polymerization activity was 14 kg-polymer/mmol-Zr.hr. This polymer contained units derived from 1-butene in amounts of 25.3% by mol, and had an intrinsic viscosity [η] of 1.89 dl/g and a melting point of 110.0° C. The proportion of the inversion bonds based on the 2,1-insertions was lower than the limit of detection.

The properties measured on the polymer are set forth in Table 1.

TABLE 1

|  | Ex. 1 | Ex. 2 | Ex. 3 | Comp. Ex. 1 |
| --- | --- | --- | --- | --- |
| 1-Butene unit content (% by mol) | 26.4 | 20.2 | 13.9 | 25.3 |
| Intrinsic viscosity [η] (dl/g) | 1.60 | 1.90 | 2.51 | 1.89 |
| Molecular weight distribution (Mw/Mn) | 2.0 | 2.0 | 1.9 | 3.5 |
| Melting point Tm (°C.) | 88.4 | 101.5 | 116.3 | 110.0 |
| Crystallinity (%) | 40 | 50 | 56 | 48 |
| B value | 1.0 | 1.0 | 1.0 | 0.94 |
| $^{13}$C-NMR (area, %) | 100 | 100 | 100 | 100 |
| Heat-sealing starting temperature (°C.) | 92 | 103 | 127 | 118 |
| Heat-sealing starting temperature (°C.) (after aging) | 97 | 107 | 131 | 131 |

TABLE 1-continued

|  | Ex. 1 | Ex. 2 | Ex. 3 | Comp. Ex. 1 |
|---|---|---|---|---|
| Martens hardness (mm$^{-1}$) | 28 | 33 | 36 | 29 |
| Blocking stress (g/cm) | 2.7 | 2.2 | 1.7 | 13 |
| Haze (%) | 3 | 4 | 3 | 3 |

EXAMPLE 4

To a 2-liter autoclave thoroughly purged with nitrogen were introduced 920 ml of hexane and 50 g of 1-butene. To the flask was added 1 mmol of triisobutylaluminum, and the temperature of the system was elevated to 70° C. Then, propylene was fed to the system so that the total pressure became 7 kg/cm$^2$-G. To the system were further added 0.28 mmol of methylaluminoxane and 0.0007 mmol (in terms of Zr atom) of rac-dimethylsilylene-bis(2-ethyl-4-phenyl-1-indenyl)zirconium dichloride, and polymerization was carried out for 30 minutes while propylene was continuously fed to keep the total pressure at 7 kg/cm$^2$-G. After the polymerization, the system was degassed and a polymer was recovered in a large amount of methanol. The polymer was vacuum dried at 110° C. for 12 hours.

The amount of the polymer obtained was 52.1 g, and the polymerization activity was 149 kg-polymer/mmol-Zr.hr. This polymer had a 1-butene content of 20.2% by mol, an intrinsic viscosity [η] of 1.90 dl/g, Mw/Mn of 2.05 and a melting point of 101.5° C.

What is claimed is:

1. A propylene elastomer having the following properties:
   (1) the elastomer contains units derived from propylene in amounts of 50 to 95% by mol and units derived from 1-butene in amounts of 5 to 50% by mol;
   (2) when (i) head-to-tail enchained propylene unit triad sequences or (ii) propylene unit-butene unit triad sequences consisting of head-to-tail enchained propylene units and butene units and containing propylene units as the second units are measured on the side chain methyl groups of the propylene units of the second units in the triad sequences using $^{13}$C-NMR spectrum (hexachlorobutadiene solution, based on tetramethylsilane), the area of peaks shown in the region of 21.0 to 21.9 ppm is not less than 90 % based on the total area of all peaks shown in the region of 19.5 to 21.9 ppm being 100%;
   (3) the elastomer has an intrinsic viscosity, as measured in decohydronophthalene at 135° C., of 0.1 to 12 dl/g;
   (4) the elastomer has a molecular weight distribution (Mw/Mn), as measured by gel permeation chromatography (GPC), of not more than 3; and
   (5) the elastomer has a parameter B value, which indicates randomness of the copolymerized monomer sequence distribution, of 1.0 to 1.5.

2. The propylene elastomer as claimed in claim 1, wherein in the property (5), the parameter B value, which indicates randomness of the copolymerized monomer sequence distribution is 1.0 to 1.3; and in addition to the properties (1) to (5), the elastomer further has the following properties:
   (6) the elastomer has a melting point Tm, as measured by a differential scanning calorimeter, of 60° to 140° C., and the melting point Tm and a 1-butene constituent unit content M (% by mol) in the elastomer satisfy the following relation:

$-2.6M+130 \leq Tm \leq -2.3M+155$ and
   (7) a crystallinity C of the elastomer, as measured by X-ray diffractometry, and a 1-butene constituent unit content M (% by mol) in the elastomer satisfy the following relation:

$C \geq -1.5M+75$.

3. The propylene elastomer as claimed in claim 1 or claim 2, said elastomer being obtained by copolymerizing propylene and 1-butene in the presence of an olefin polymerization catalyst comprising:

[A] a transition metal compound represented by the following formula [I]:

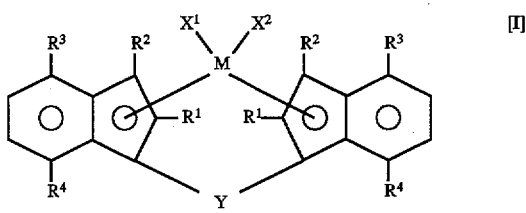

wherein M is a transition metal of Group IVa, Group Va or Group VIa of the periodic table, $R^1$ and $R^2$ are each a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group, $R^3$ is a secondary or tertiary alkyl group of 3 to 20 carbon atoms or an aromatic group, $R^4$ is a hydrogen atom or an alkyl group of 1 to 20 carbon atoms, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, SO—, —SO$_2$—, —NR$^5$—, —P(R$^5$)—, —P(O)(R$^5$)—, —BR$^5$— or —AlR$^5$— (R$^5$ is a hydrogen atom, a halogen atom, a hydrocarbon group of 1 to 20 carbon atoms or a halogenated hydrocarbon group of 1 to 20 carbon atoms);

and

[B] [B-1] an organoaluminum oxy-compound, and/or

[B-2] a compound which reacts with the transition metal compound [A] to form an ion pair;

and optionally

[C] an organoaluminum compound.

4. The propylene elastomer as claimed in claim 3, wherein $R^1$ in the formula [I] representing the transition metal compound [A] is a methyl group.

5. The propylene elastomer according to claim 1 which is obtained by copolymerizing propylene and 1-butene in the presence of an olefin polymerization catalyst comprising:

[A] a transition metal compound represented by the following formula [I-a]:

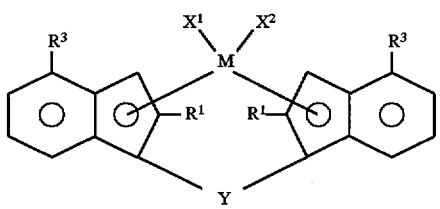

wherein M is a transition metal of Group IVa, Group Va or Group VIa of the periodic table, R$^1$ is a hydrocarbon group of 2 to 6 carbon atoms, R$^3$ is an aryl group of 6 to 16 carbon atoms which may be substituted with a halogen atom, a hydrocarbon group of 1 to 20 carbon atoms or a silyl group, X$^1$ and X$^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, SO—, —SO$_2$—, —NR$^5$—, —P(O) (R$^5$)—, —BR$^5$— or —AlR$^5$— (R$^5$ is a hydrogen atom, a halogen atom, a hydrocarbon group of 1 to 20 carbon atoms or a halogenated hydrocarbon group of 1 to 20 carbon atoms);

and

[B] at least one compound selected from the group consisting of:

[B-1] an organoaluminum oxy-compound, and

[B-2] a compound which reacts with the transition metal compound [A] to form an ion pair.

6. A propylene elastomer according to claim 1 having the following properties:

(1) from 70 to 90% by mole of units derived from propylene and from 10 to 30% by mole of units derived from 1-butene;

(2) the area of peaks shown in the region of 21.0 to 21.9 ppm is not less than 94% based on the total area of all peaks shown in the region of 19.5 to 21.9 ppm being 100%;

(3) an intrinsic viscosity measured in decahydronaphthalene, at 135° C., of from 1 to 12 dl/g;

(4) a molecular weight distribution (Mw/Mn), as measured by gel permeation chromatography, of from 2.0 to 2.5;

(5) a B value of from 1.0 to 1.2.

7. A propylene elastomer according to claim 6 further characterized by:

(6) a melting point, Tm, as measured by a differential scanning calorimeter, of 80° to 130° C., and the melting point and the 1-butene constituent unit content M (% by mole) satisfying the following relation:

$$-2.6M+130 \leq Tm \leq -2.3M+155;$$

(7) a crystallinity, C, as measured by X-ray diffractometry, and a 1-butene constituent unit content M in the elastomer satisfying the following relationship:

$$C \geq -1.5M+75.$$

8. A propylene elastomer according to claim 1 having the following properties:

(1) a 1-butene unit content in the range from about 13.9 to 26.4% by mole;

(2) an intrinsic viscosity of from about 1.60 to 2.51 dl/g;

(3) a molecular weight distribution of from about 1.9 to about 2.05;

(4) a B value of about 1.0;

a heat-sealing starting temperature in the range from about 92° to about 127° C.;

a heat-sealing starting temperature, after aging, of from about 97° to about 131° C.;

a Martens hardness of from about 28 to 35 mm$^{-1}$;

a blocking stress of from about 2.7 to 1.7 g/cm;

a haze from about 3% to 4%.

* * * * *